United States Patent
Longo et al.

(10) Patent No.: US 11,957,609 B2
(45) Date of Patent: Apr. 16, 2024

(54) DEPLOYMENT HANDLE FOR DELIVERY OF IMPLANTS

(71) Applicant: Intact Vascular, Inc., Wayne, PA (US)

(72) Inventors: Michael A. Longo, Glenmoore, PA (US); Chad J. Smith, Phoenixville, PA (US); Igor Tentler, Jamison, PA (US); Michael A. Dotsey, Chester Springs, PA (US); Evan E. Aamodt, Philadelphia, PA (US); Leif E. Malm, Elverson, PA (US); Kevin Y. Shin, Lowell, MA (US); Erin H. Morrissey, Mont Claire, PA (US); Patrick B. Nolan, Royersford, PA (US); Noah E. Dingler, Phoenixville, PA (US)

(73) Assignee: INTACT VASCULAR, INC., Wayne, PA (US)

( * ) Notice: Subject to any disclaimer, the term of this patent is extended or adjusted under 35 U.S.C. 154(b) by 378 days.

(21) Appl. No.: 17/128,790

(22) Filed: Dec. 21, 2020

(65) Prior Publication Data

US 2021/0196494 A1 Jul. 1, 2021

Related U.S. Application Data

(60) Provisional application No. 62/955,254, filed on Dec. 30, 2019.

(51) Int. Cl.
 *A61F 2/966* (2013.01)
 *A61F 2/95* (2013.01)
 *A61M 39/00* (2006.01)

(52) U.S. Cl.
 CPC ............ *A61F 2/966* (2013.01); *A61F 2/9517* (2020.05); *A61M 2039/0018* (2013.01)

(58) Field of Classification Search
 CPC .. A61F 2/966; A61F 2/9517; A61F 2002/826; A61F 2/95; A61F 2/958; A61M 2039/0018
 See application file for complete search history.

(56) References Cited

U.S. PATENT DOCUMENTS

| 10,449,073 B1 | 10/2019 | Longo |
| 2005/0273151 A1 | 12/2005 | Fulkerson |

(Continued)

FOREIGN PATENT DOCUMENTS

| WO | 2016/123509 | 8/2016 |
| WO | 2019232029 A1 | 12/2019 |

OTHER PUBLICATIONS

International Search Report and Written Opinion dated Apr. 13, 2021 for International Application No. PCT/US2020/066344 Filed Dec. 21, 2020, 8 pages.

*Primary Examiner* — Kelly J Bekker
*Assistant Examiner* — Andrew P. Restaino

(57) ABSTRACT

A delivery device for controllably delivering multiple implants (e.g., intravascular implants) is described herein. The delivery device may include a lockout mechanism to prevent against inadvertent implant deployment prior to initial use. The delivery device may also include a re-sheath mechanism to allow for re-sheathing of an inner core assembly prior to removal of the delivery device from an initial deployment site. The delivery device may also further include a mechanism configured to prevent against re-sheathing of a partially-deployed implant.

15 Claims, 18 Drawing Sheets

(56) References Cited

U.S. PATENT DOCUMENTS

| | | | |
|---|---|---|---|
| 2009/0105798 A1* | 4/2009 | Koch | A61F 2/95 623/1.11 |
| 2009/0210046 A1 | 8/2009 | Shumer | |
| 2010/0004606 A1 | 1/2010 | Hansen | |
| 2013/0018451 A1* | 1/2013 | Grabowski | A61F 2/966 623/1.11 |
| 2014/0155982 A1* | 6/2014 | Gerdts | A61F 2/966 623/1.12 |
| 2015/0297378 A1* | 10/2015 | Senness | A61F 2/966 623/1.11 |
| 2015/0335452 A1* | 11/2015 | Rao | A61F 2/966 623/23.66 |
| 2015/0359997 A1 | 12/2015 | Crisostomo | |
| 2016/0074184 A1 | 3/2016 | Cummins | |
| 2016/0256307 A1* | 9/2016 | Longo | A61M 25/104 |
| 2018/0000619 A1 | 1/2018 | Longo | |
| 2018/0153693 A1* | 6/2018 | Copeland | A61F 2/2436 |
| 2018/0168838 A1* | 6/2018 | Kratzberg | A61F 2/966 |

\* cited by examiner

DEPLOYMENT HANDLE FOR DELIVERY OF IMPLANTS

INCORPORATION BY REFERENCE

This application claims priority benefit of U.S. Provisional Patent Application No. 62/955,254 filed Dec. 30, 2019, which is incorporated herein by reference in its entirety for all purposes.

FIELD

The disclosure relates to devices and methods that can be used to deploy one or more implants within a subject, such as, but not limited to, intravascular implants for treating vascular dissections within a vascular system of a subject.

BACKGROUND

There are a number of medical conditions and procedures in which an implant such as a stent is placed in the body to create or maintain a passage. There are a wide variety of stents used for different purposes, from expandable coronary, vascular and biliary implants, to plastic stents used to allow the flow of urine between kidney and bladder.

Stents are often placed in the vascular system after a medical procedure, such as balloon angioplasty. Balloon angioplasty is often used to treat atherosclerotic occlusive disease. Atherosclerotic occlusive disease is the primary cause of stroke, heart attack, limb loss, and death in the US and the industrialized world. Atherosclerotic plaque forms a hard layer along the wall of an artery and can be comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty, which may be followed with stent placement.

SUMMARY

The disclosure relates generally to devices and associated methods for delivering at least one implant (e.g., an expandable stent) and, in certain arrangements, devices and associated methods for delivering multiple implants (e.g., expandable stents) at various target sites within a subject (e.g., within a diseased blood vessel). The disclosure includes a deployment handle of a delivery device (e.g., delivery catheter) that is designed to mechanically retract an outer sheath of the delivery catheter in a controlled manner so as to facilitate delivery, or deployment, of an implant or multiple implants loaded on an inner core of the delivery catheter at various spaced-apart locations (e.g., locations within a single blood vessel, locations within multiple different blood vessels, or multiple other locations in other body passages or lumens) within the subject. The deployment handle may include an ergonomic design that facilitates gripping of the deployment handle by a single hand of an operator. The deployment handle advantageously improves ease of use by allowing a simple single-handed operation of the deployment mechanism by an operator, while maintaining appropriate deployment accuracy of the multiple implants and mitigating potential for inadvertent, premature deployment of the implants. The deployment handle also advantageously allows the operator to easily deploy any additional remaining implants from the delivery catheter after re-sheathing of the inner core has been performed at a first target site (either at the same target site or a different target site).

In accordance with several embodiments of the disclosure, the deployment handle advantageously includes a lockout assembly configured to prevent, or reduce the likelihood of, premature, unintended deployment, or delivery, of any of the implants until the operator intentionally disables a lockout mechanism to enable deployment. The lockout assembly advantageously provides a safety feature that prevents against, or reduces the likelihood of, inadvertent deployment of any of the implants from a time of manufacture until the delivery catheter has been advanced to an appropriate target treatment site within the subject. In accordance with several embodiments of the disclosure, the lockout assembly (e.g., a lockout lever of the lockout assembly) provides a further benefit of acting as a tensioner upon disengagement of the lockout mechanism. The lockout mechanism may advantageously be disengaged (e.g., meaning that the device is ready for use) with a single step/action performed by the operator (e.g., pressing down, or inward, on a lockout lever of the lockout assembly) that may also be performed using a single finger or thumb of the operator.

Several embodiments of the deployment handle may include a deployment or actuation assembly or mechanism (such as a thumbwheel and belt assembly or a slider assembly) configured to facilitate un-sheathing of an outer sheath of the delivery catheter to deploy one or more implants from an inner core of the delivery catheter. The deployment or actuation assembly or mechanism may be configured in a manner that only allows un-sheathing and not re-sheathing. For example, if the deployment or actuation assembly or mechanism includes a thumbwheel and belt assembly, the deployment handle may advantageously include a "reverse scrolling prevention" feature that only allows the thumbwheel and belt assembly to rotate in one rotational direction (e.g., clockwise) and to prevent rotation in the opposite rotational direction (e.g., counter-clockwise), thereby further mitigating against inadvertent deployment of implants, or damage to the implants or body tissue (e.g., vessel wall) of the subject. The deployment or actuation assembly or mechanism may also provide tactile and/or audible feedback to the user (e.g., clicking that can be felt and heard) during operation of the deployment or actuation assembly (e.g., signifying that un-sheathing is occurring and a rate at which the un-sheathing is occurring).

In accordance with several embodiments of the disclosure, following deployment of one or more initial implants, the operator can re-sheath a distal end of the delivery catheter using the deployment handle by actuating a re-sheath button of the deployment handle and pulling back (e.g., in a proximal direction away from a main housing body of the deployment handle and toward the operator) on a re-sheath housing located at the proximal end of the deployment handle. The deployment handle may advantageously be configured to prevent operation of a deployment mechanism of the deployment handle during the act of re-sheathing to prevent, or reduce the likelihood of, inadvertent deployment of an implant and/or damage to the implant(s) or to body tissue (e.g., vessel wall) of the subject.

Once the delivery catheter has been removed from a first target treatment site (or entirely from the body of the subject), the operator has the option to re-insert the delivery catheter to another target treatment site if there are still implants loaded within the delivery catheter. To perform this operation, the operator can, for example, guide the delivery catheter to the new target treatment site, actuate the re-sheath button with one hand and push on the re-sheath housing with the other hand (e.g., in a distal direction toward the main housing body of the deployment handle away from the operator) until the re-sheath housing engages again with the main housing body of the deployment handle. This operation un-sheaths an inner core assembly of the delivery catheter to the same spot, position, or configuration where it left off before re-sheathing was performed after the initial implant deployment(s) at the first target treatment site. The deployment handle may then be used to facilitate delivery of any of the additional remaining implants at the new target treatment site.

In accordance with several embodiments of the disclosure, the deployment handle includes flush ports to facilitate flushing of various lumens of the delivery catheter prior to insertion within the subject so as to prevent, or reduce the likelihood of, air bubbles or pockets from being delivered within the subject (e.g., within vasculature of the subject) and/or to increase lubricity. The various internal components of the delivery catheter may be specifically configured to facilitate multiple fluid pathways through all of the multiple lumens and spaces of the delivery catheter in such a manner that the flushing fluid travels all the way to the distal terminus of the delivery catheter and such that no air bubbles or pockets may be retained in lumens, spaces or gaps within the delivery catheter and/or to increase lubricity after appropriate flushing.

In accordance with several embodiments of the disclosure, a delivery device (e.g., delivery catheter) for delivering one or more implants includes an inner shaft comprising a proximal end and a distal end. The delivery device further includes an outer sheath having a proximal end, a distal end, and a lumen extending from the proximal end of the outer sheath to the distal end of the outer sheath. The outer sheath is moveable relative to the inner shaft and/or vice-versa. The delivery device also includes a deployment handle (e.g., a rotary deployment handle) configured to cause movement of the outer sheath relative to the inner shaft so as to facilitate delivery of an implant or multiple implants carried by the inner shaft at spaced-apart locations (e.g., within a single treatment zone, such as a portion of a blood vessel, or within multiple different treatment zones, such as different blood vessels). The handle includes a deployment actuator (e.g., a thumbwheel configured to be rotated by a user in a first rotational direction or a slider mechanism configured to be slid forward and backward or a trigger button configured to be pressed) configured to effect movement of the outer sheath relative to the inner shaft to unsheath a portion of the inner shaft.

In some embodiments of the disclosure, the handle further includes a lockout assembly configured to prevent rotation of the thumbwheel until the lockout assembly is actuated by an operator (e.g., with a single step or operation as opposed to multiple steps or operations) to cause the thumbwheel to transition from a locked configuration (e.g., a configuration in which movement of the outer sheath relative to the inner shaft is not possible, or is prevented) to an unlocked configuration (e.g., a configuration in which movement of the outer sheath relative to the inner shaft is possible, or is not prevented).

The inner shaft of the delivery device may optionally include a lumen extending from the proximal end to the distal end of the inner shaft so as to facilitate over-the-wire tracking over a guidewire. The inner shaft may alternatively include a lumen that extends only along a portion of a length of the inner shaft (e.g., rapid exchange-type configuration).

In some embodiments of the disclosure, the thumbwheel is configured to only rotate in the first rotational direction and not in the opposite rotational direction.

In some embodiments of the disclosure, the delivery device optionally includes a re-sheath assembly configured to facilitate manual re-sheathing of the inner shaft by pulling a re-sheath housing that is coupled to the inner shaft in a proximal direction, thereby moving the inner shaft relative to the outer sheath.

In accordance with several embodiments of the disclosure, a delivery device for delivering one or more implants includes an inner shaft comprising a proximal end and a distal end. The delivery device further includes an outer sheath having a proximal end, a distal end, and a lumen extending from the proximal end of the outer sheath to the distal end of the outer sheath. The outer sheath is moveable relative to the inner shaft and/or vice-versa. The delivery device further includes a rotary deployment handle configured to cause movement of the outer sheath relative to the inner shaft so as to facilitate delivery of at least one implant carried by the inner sheath at spaced-apart locations. The deployment handle includes a thumbwheel configured to be rotated by a user in a first rotational direction to effect movement of the outer sheath relative to the inner shaft to unsheath a portion of the inner shaft. The thumbwheel is configured to only rotate in the first rotational direction (e.g., clockwise) and not in the opposite rotational direction (e.g., counter-clockwise).

In accordance with several embodiments of the disclosure, a delivery device (e.g., delivery catheter) for delivering one or more implants includes the inner shaft and outer sheath as described above. The delivery device also includes a deployment handle configured to cause movement of the outer sheath relative to the inner shaft so as to facilitate delivery of at least one implant carried by the inner sheath. The delivery device further includes a re-sheath assembly configured to facilitate re-sheathing of the inner shaft by manual pulling of a re-sheath housing that is coupled to the inner shaft in a proximal direction, thereby moving the inner shaft relative to the outer sheath. In other configurations, the re-sheath housing may be coupled to the outer sheath such that the outer sheath may move relative to the inner shaft in order to re-sheath.

The delivery device may further include a deployment actuator, such as a thumbwheel, configured to be rotated by a user in a first rotational direction to effect movement of the outer sheath relative to the inner shaft to un-sheath a portion of the inner shaft. The thumbwheel may be coupled to a belt/pulley assembly. The delivery device may optionally be preloaded with one or more implants on the inner shaft.

In accordance with several embodiments of the disclosure, a delivery device (e.g., delivery catheter) for delivering multiple implants includes an inner shaft and an outer sheath and a lumen extending from the proximal end of the outer sheath to the distal end of the outer sheath within which the inner shaft resides. The delivery device further includes a deployment handle configured to cause movement of the outer sheath relative to the inner shaft so as to facilitate delivery of multiple implants carried by the inner shaft at spaced-apart locations. The deployment handle includes an elongated main housing comprising a proximal end and a distal end and an upper surface. The deployment handle also includes a deployment actuator configured to cause the movement of the outer sheath relative to the inner shaft. The deployment handle further includes a re-sheath assembly configured to facilitate re-sheathing of the inner shaft prior to removal of the delivery device from a treatment zone (or complete removal from the body) within a subject after deployment of one or more of the multiple implants at the treatment zone. The re-sheath assembly includes a re-sheath housing removably coupled to the proximal end of the main housing of the rotary deployment handle, a re-sheath button located adjacent to the proximal end of the main housing distal to the re-sheath housing, and a re-sheath rack located within the main housing of the rotary deployment handle. A proximal end of the re-sheath rack may be fixedly (e.g., permanently) coupled to the re-sheath housing and the inner shaft may be operably coupled to the re-sheath housing such that retraction of the re-sheath housing in a proximal direction away from the main housing causes the re-sheath rack and the inner shaft to move in a proximal direction, thereby re-sheathing the inner shaft within the outer sheath.

In some embodiments of the disclosure, the re-sheath button is configured to prevent longitudinal movement of the re-sheath housing and re-sheath rack unless the re-sheath button is pressed into the main housing by the operator. The deployment actuator may include a thumbwheel extending out of the upper surface of the main housing. The thumbwheel may include a plurality of teeth configured to engage with links of a belt that is operatively coupled to the outer sheath so as to effect movement of the outer sheath relative to the inner shaft when the thumbwheel is rotated. In some embodiments of the disclosure, movement of the re-sheath rack in a proximal direction during re-sheathing causes the thumbwheel to transition to be placed in a locked configuration such that rotation of the thumbwheel is prevented during re-sheathing. The delivery device may optionally include one or more flush ports extending outward from a proximal end of the re-sheath housing to facilitate flushing of the lumens of the inner shaft and the outer sheath. The inner shaft of the delivery device may include a lumen extending from the proximal end to the distal end (e.g., to facilitate tracking of the delivery device over a guidewire).

In accordance with several embodiments of the disclosure, a delivery device for delivering one or more implants includes an inner shaft comprising a proximal end and a distal end. The delivery device further includes an outer sheath having a proximal end, a distal end, and a lumen extending from the proximal end of the outer sheath to the distal end of the outer sheath. The delivery device also includes a rotary deployment handle configured to cause movement of the outer sheath relative to the inner shaft so as to facilitate delivery of at least one implant (e.g., one implant, two implants, three implants, four implants, more than four implants) carried by the inner shaft. The rotary deployment handle includes a thumbwheel and a belt and pulley assembly operably coupled to the thumbwheel and to the outer sheath such that rotation of the thumbwheel causes movement of the outer sheath relative to the inner shaft. The rotary deployment handle also includes a lockout assembly configured to: (a) cause the thumbwheel to transition from a locked configuration in which the thumbwheel is unable to rotate to an unlocked configuration in which the thumbwheel is able to rotate and (b) sufficiently tension the belt during the transition from the locked configuration to the unlocked configuration.

The deployment assembly may further include a shuttle, or belt link, surrounding a portion of a length of the outer sheath. The shuttle may be bonded to the outer sheath and be configured to mate, or engaged with the belt so as to effect movement of the outer sheath as the belt moves in response to rotation of the thumbwheel.

In some embodiments of the disclosure, the deployment handle further includes a ratchet wheel comprising teeth configured to operably couple to teeth of the thumbwheel. An angle of the teeth of the thumbwheel and the ratchet wheel may be shaped and configured to prevent rotational movement of the thumbwheel in the opposite rotation direction (e.g., counter-clockwise) of a normal operative rotation direction (e.g., clockwise). In some embodiments of the disclosure, the deployment handle includes a ratchet wheel comprising teeth configured to operably couple to teeth of the thumbwheel in a manner so as to create tactile feedback and/or audible clicks to an operator as the thumbwheel is rotated by the operator. The audible clicks may indicate a rate (e.g., speed) of unsheathing to the operator, thereby allowing the operator to slow down the unsheathing if desired.

In some embodiments of the disclosure, the lockout assembly includes a lockout lever (e.g., shelf lockout). The lockout lever includes a proximal end portion configured to extend out of a main housing of the rotary deployment handle when the lockout assembly is in a locked configuration and a distal end fixedly coupled to the main housing of the rotary deployment handle. The lockout lever may hide the thumbwheel when the lockout lever is in the locked configuration.

The lockout assembly may further include a lockout plate comprising a proximal abutment surface configured to interface with a protrusion (e.g., nub) of the lockout lever. The lockout plate may also include multiple engagement members (e.g., heads) configured to interface with one or more recesses between the gear teeth of the thumbwheel so as to prevent rotation of the thumbwheel when the lockout assembly is in the locked configuration. The lockout plate may be biased to move toward a proximal end of the rotary deployment handle by a spring (e.g., torsion spring) or other biasing member, such as an elastic strap.

In some implementations, upon depression of the proximal end of the lockout lever into the main housing by an operator, the lockout assembly transitions to the unlocked configuration by causing the protrusion of the lockout lever to disengage from the proximal abutment surface of the lockout plate, thereby causing the lockout plate to move proximally (as it is biased to do by the spring) so as to allow a proximal engagement member of the multiple engagement members (e.g., heads) of the lockout plate to disengage from the thumbwheel (e.g., the gear teeth/recesses) and thereby allow the thumbwheel to rotate.

In some embodiments of the disclosure, the delivery device further includes a re-sheath assembly configured to facilitate re-sheathing of the inner shaft prior to removal of the delivery device from a delivery location within a subject. The re-sheath assembly may include a re-sheath housing removably coupled to a proximal end of the main housing of the rotary deployment handle, a re-sheath button located adjacent the proximal end of the main housing distal to the re-sheath housing, and a re-sheath rack located within the main housing of the rotary deployment handle.

In some embodiments of the disclosure, the re-sheath button is configured to prevent longitudinal movement of the re-sheath housing and re-sheath rack unless the re-sheath button is pressed into the main housing by the operator. A proximal end of the re-sheath rack may be fixedly coupled (e.g., permanently attached) to the re-sheath housing and the inner shaft may be operably coupled to the re-sheath housing such that retraction of the re-sheath housing in a proximal direction away from the main housing causes the re-sheath rack and the inner shaft to move in a proximal direction, thereby re-sheathing the inner shaft within the outer sheath.

An engagement protrusion at a distal end of the lockout plate may be configured to engage with the distal end of the re-sheath rack such that when the re-sheath rack is in a distal-most position within the main housing, the lockout plate is prevented from moving proximally. In some implementations, upon movement of the re-sheath rack in a proximal direction during re-sheathing, the engagement protrusion at the distal end of the lockout plate is no longer constrained from proximal movement by the distal end of the re-sheath rack, and therefore moves in a proximal direction until a distal engagement member of the lock-out plate engages with one or more recesses between the teeth of the thumbwheel, thereby preventing rotation of the thumbwheel during re-sheathing. As mentioned before, the lockout plate may be biased to move in the proximal direction by the spring or other biasing member.

The rotary handle may also include multiple flush ports extending outward from a proximal end of the rotary deployment handle to facilitate flushing of the lumens of the inner shaft and the outer sheath. The inner shaft may include a lumen (e.g., a guidewire lumen) extending from the proximal end to the distal end of the inner shaft so as to facilitate over-the-wire delivery. The inner shaft may include a plurality of delivery platforms disposed along the inner shaft toward the distal end, each of the plurality of delivery platforms including a recess extending distally of a radial protrusion.

A system may include a delivery device as described herein in combination with multiple implants. Each of the multiple implants may be disposed about a corresponding delivery platform of the plurality of delivery platforms. The system may be configured to place at least two implants of the plurality of implants at a treatment zone at spaced apart locations such that a minimum gap is provided in the treatment zone between a distal end of a proximal implant and a proximal end of a distal implant without requiring the plurality of delivery platforms to be moved between deployment of the at least two implants. The multiple implants may include at least two implants that are identical or all of the multiple implants may be identical. The multiple implants may include implants of different shapes or sizes (e.g., lengths).

In accordance with several embodiments of the disclosure, a method of delivering implants at multiple different treatment sites within a subject includes advancing a delivery catheter to a first treatment site within the subject. The delivery catheter includes an inner shaft and an outer sheath concentrically surrounding the inner shaft. The inner shaft and the outer sheath are configured to move relative to each other (e.g., one can translate axially forward or backward with respect to the other). The inner shaft may be loaded (during manufacture or before use) with a plurality of implants at spaced-apart locations along the length of the inner shaft. The method further includes deploying a first one or more implants (e.g., two implants) at the first treatment site within the subject by un-sheathing the first one or more implants by moving the outer sheath proximally while the inner shaft remains stationary. The method also includes re-sheathing the portion of the inner shaft corresponding to the locations of the deployed first one or more implants by moving the inner shaft proximally while the outer sheath remains stationary, thereby facilitating improved safety to the subject while the delivery catheter is moved to a second treatment site within the subject. The re-sheathing may be effected by the operator pulling a re-sheath housing of the rotary deployment handle in a proximal direction. The method further includes advancing the delivery catheter to the second treatment site within the subject and un-sheathing the portion of the inner shaft corresponding to the locations of the deployed first one or more implants by moving the inner shaft distally while the outer sheath remains stationary such that a distal end of the outer sheath is at the same distance away from the distal end of the inner shaft as it was after deployment of the first one or more implants. The un-sheathing may be effected by the operator pushing the re-sheath housing of the rotary deployment handle in a distal direction. The method may also include deploying a second one or more implants (e.g., two implants) at the second treatment site within the subject by un-sheathing the second one or more implants by moving the outer sheath proximally while the inner shaft remains stationary. The un-sheathing may be effected by rotation of the thumbwheel by the operator.

The implants may include, but are not limited to, self-expandable endovascular implants. The first treatment site may be a location of one or more first vascular dissections and the second treatment site may be a location of one or more second vascular dissections. The first treatment site and the second treatment site may be in the same blood vessel or in different blood vessels (e.g., arteries, veins, capillaries). Implants may be delivered to more than two treatment sites. The treatment sites may be located above the knee or below the knee. The treatment sites are not limited to the leg but can include locations in the arms, coronary vasculature, neurovasculature, peripheral vasculature, coronary vasculature, or other vasculature. The treatment sites may alternatively be located in other body lumens, channels, passageways other than vasculature.

BRIEF DESCRIPTION OF THE DRAWINGS

Various embodiments are depicted in the accompanying drawings for illustrative purposes and should in no way be interpreted as limiting the scope of the inventions, in which like reference characters denote corresponding features consistently throughout similar embodiments.

FIGS. 7A and 7B illustrate side views of various internal components when a thumbwheel is in a locked configuration. FIGS. 7C and 7D illustrate side views of various internal components when the thumbwheel is in an unlocked configuration.

FIG. 9 shows various internal components involved in a re-sheathing function of the rotary deployment handle.

DETAILED DESCRIPTION

A. Introduction

Figure 1:
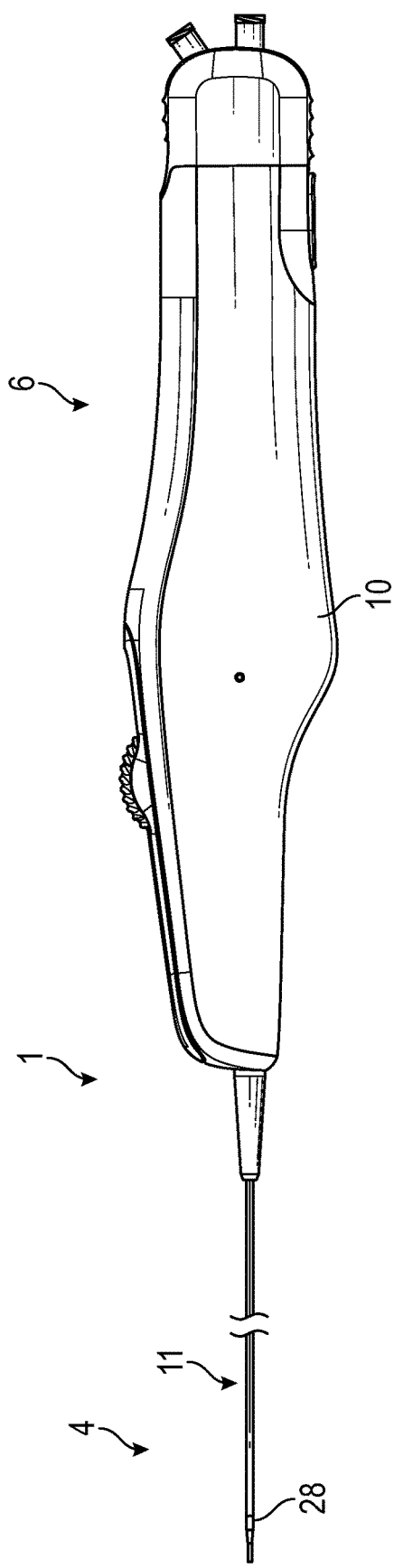
FIG. 1 is a side view of a delivery device for delivering multiple implants in a controlled manner.

Devices and associated methods for delivering an implant (e.g., an expandable stent) and/or multiple implants (e.g., expandable stents) at various target sites within a subject (e.g., within a diseased blood vessel) are described herein according to several embodiments of the disclosure. The disclosure includes a description of structural components and functionality of various configurations or implementations of a rotary deployment handle of a delivery device (e.g., delivery catheter) that is designed to mechanically retract an outer sheath of the delivery catheter in a controlled manner so as to facilitate delivery, or deployment, of a single implant or multiple implants at various spaced-apart locations (e.g., locations within a single blood vessel, locations within multiple different blood vessels, or multiple other locations in other body passages or lumens) within the subject.

Several embodiments of the disclosure are particularly advantageous because they include one, several or all of the following benefits: (i) improved ease of use by allowing a simple single-handed operation of the deployment mechanism by an operator, (ii) maintained appropriate deployment accuracy of multiple implants; (iii) mitigation of potential for inadvertent, premature deployment of the implants; (iv) efficient and simple deployment of remaining implants from the delivery catheter after re-sheathing has been performed (either at the same target site or a different target site); (v) reduced likelihood of inadvertent re-sheathing of a partially-deployed implant; (vi) reduced likelihood of damage to implants or body tissue; (vii) prevention of deployment or delivery of any of the implants until the operator intentionally disables a shelf lockout mechanism to enable initial implant deployment; (viii) increased lubricity of the delivery catheter; and/or (ix) reduced likelihood of air bubbles being introduced into vasculature of a subject through the delivery catheter.

Several configurations of a deployment handle of the delivery catheter may include a thumbwheel and belt assembly configured to facilitate un-sheathing of an outer sheath to deploy the implants from an inner core of the delivery catheter. The deployment handle may advantageously include a feature that only allows the thumbwheel and belt assembly to rotate in one rotational direction (e.g., clockwise) and to prevent rotation in the opposite rotational direction (e.g., counter-clockwise), thereby further mitigating against inadvertent deployment of implants, or damage to the implants or body tissue (e.g., vessel wall) of the subject. The deployment handle may further include a lockout assembly configured to prevent rotation of the thumbwheel until the lockout assembly is actuated by an operator to cause the thumbwheel to transition from a default locked configuration (as set during initial manufacture or assembly) to an unlocked configuration in which implants may be deployed. The lockout mechanism may be disengaged by performance of a simple, single step or operation by the operator.

In accordance with several implementations, following deployment of one or more initial implants, the operator can re-sheath a distal end of the delivery catheter (exposed areas of previously-deployed implants) using the deployment handle by actuating a re-sheath button of the deployment handle and pulling back (e.g., in a proximal direction away from a main housing body of the deployment handle, or toward the operator) on a re-sheath housing. The deployment handle may advantageously be configured to prevent operation of a deployment mechanism of the deployment handle during the act of re-sheathing, again preventing, or reducing the likelihood of, inadvertent deployment of an implant and/or damage to the implants or body tissue (e.g., vessel wall) of the subject.

Once the delivery catheter has been removed from a first target treatment site or entirely from the body of the subject, the operator has the option to re-insert the delivery device to another target treatment site if there are still implants loaded within the delivery catheter, or after insertion of additional implants. The deployment handle may then be used to facilitate delivery of any of the additional remaining implants. A re-sheathing process may facilitate re-positioning of the distal tips of the inner shaft and outer sheath to their respective positions prior to unsheathing during the deployment of the initial implant(s), thereby facilitating efficiency and ease of use.

B. Delivery Catheter

FIG. 1 illustrates an embodiment of a delivery device 1 that can be used for sequential delivery of multiple implants 2 in a controlled manner. The delivery device 1 may also be referred to herein as a delivery catheter. In accordance with several implementations, the delivery device 1 can be used in procedures to treat atherosclerotic occlusive disease, though it is not limited to these procedures. The delivery device 1 can be used to deliver one or more implants 2 to a site of plaque accumulation (e.g., one, two, three, four, or more than four implants). The implants 2 can stabilize the site and/or hold pieces of plaque out of the way of blood flow. It will be understood that though the delivery devices and methods described herein are described primarily with reference to vascular procedures and to treating vascular dissections, they can also be used in treatments for other conditions and other parts of the body. In addition, while the delivery device 1 has certain features that are particularly useful for delivering multiple implants certain features of delivery device can be used in a device configured to deliver a single implant.

The delivery device 10 of FIG. 1, which has been shortened to facilitate illustration, highlights the distal end portion 4 and the proximal end portion 6 of the delivery device 1. The length of the delivery device 1 may vary as required and/or desired. In various implementations, the length may range from 50 cm to 250 cm (e.g., from 50 cm to 100 cm, from 80 cm to 120 cm, from 100 cm to 200 cm, from 120 cm to 180 cm, from 140 cm to 160 cm, from 150 cm to 250 cm, from 180 cm to 220 cm, from 200 cm to 250 cm overlapping ranges thereof, or any value within the recited ranges). The proximal end portion 6 comprises a deployment handle 10 that can be held in a single hand of a physician or other medical professional during a medical procedure. The proximal end portion 6 can be configured in a variety of manners such as, for example, an integrated handle assembly (as illustrated) or a "pin and pull" configuration (not illustrated). The deployment handle 10 can be used to control delivery (e.g., sequential delivery or simultaneous delivery) of one or more of the implants 2. The delivery device 1 further includes a catheter assembly 11 extending from the deployment handle 10 to the distal end portion 4 of the delivery device 1. The delivery device 1 may optionally include a strain relief 30 to facilitate a transition between the deployment handle 10 and the catheter assembly 11. The strain relief 30 can take a variety of forms and be composed of a variety of materials, such as being made of polyolefin or other similar material.

Figure 2:
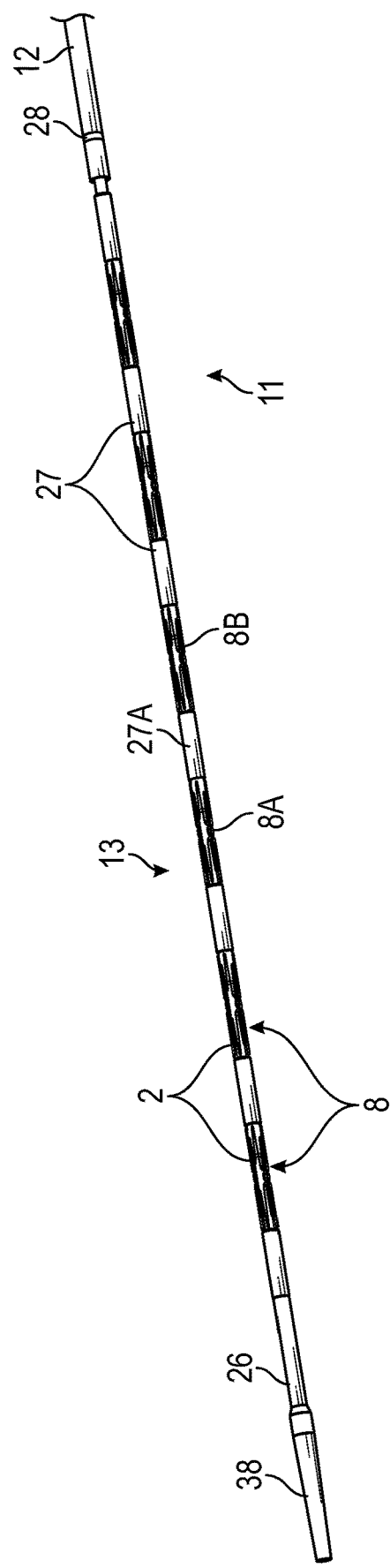
FIG. 2 shows a view of the distal end of the delivery device of FIG. 1 with an outer sheath retracted to show multiple implants loaded on an inner shaft of the delivery device.

FIG. 2 shows the distal end portion 4 of the delivery device 1 and the catheter assembly 11. The catheter assembly 11 includes an outer sheath 12 and an inner core assembly 13. As shown, the inner core assembly 13 is loaded with six implants 2, each positioned at a dedicated delivery platform 8. While FIGS. 1 and 2 illustrate a delivery device 1 with six implants and six dedicated delivery platforms, the delivery device 1 can include more or less implants 2 and delivery platforms 8 (such as 1, 2, 3, 4, 5, 7, 8 or more than 8) implants 2 and delivery platforms 8. The inner core assembly 13 may include one or more components. For example, the inner core assembly 13 may include an elongated inner shaft 26 comprising a lumen configured to facilitate coaxial advancement over a guidewire and a pusher tube 29 (shown in FIG. 5) concentrically surrounding (e.g., coaxial with) the elongated inner shaft 26. The pusher tube 29 may comprise polyetheretherketone (PEEK) tubing in some implementations. However, other polymers or metals may also be used. The inner core assembly 13 may also include a delivery tube (e.g., delivery tube 51 described elsewhere herein).

Comparing FIGS. 1 and 2, it can be seen that the outer sheath 12 has been withdrawn from a distal terminus of the delivery device 1 in FIG. 2. This withdrawing of the outer sheath 12 reveals the delivery platforms 8 and the respective implants 2 loaded on the inner core assembly 13. The implants 2 can be self-expandable and are shown in their compressed position, state, or configuration, to represent how they would fit in the delivery platforms. In use, the outer sheath 12 can cover the implants 2 when in this compressed position, state, or configuration. The outer sheath 12 can be withdrawn in a systematic, controlled manner to deploy one implant 2 at a time at one or more desired treatment locations or sites, as the implants 2 may self-expand once unsheathed from the outer sheath 12. Advantageously, the delivery device 1 can be used to implant relatively small implants that can be delivered at precise treatment locations and spaced appropriately so as to not overlap. It will be understood, that the delivery devices and methods can also be used for other medical devices, including larger devices, and are not limited to use with the intraluminal, or endovascular, implants 2 described herein.

As shown in FIG. 2, the delivery catheter can include a distal tip 38 comprising a tapered nose cone and can be made of a soft material. In accordance with several implementations, the tip 38 may advantageously serve as a dilating structure to atraumatically displace tissue and help to guide the delivery catheter 1 through the vasculature or other body lumen, passage or channel. The tip 38 itself may be radiopaque, or comprise a radiopaque element (not shown) and be incorporated into or near the tip.

Parts of one of the delivery platforms 8 are also shown in FIG. 2. The delivery platforms 8 can be identical or substantially identical, though other embodiments of the disclosure can have delivery platforms 8 of different sizes and constructions between different delivery platforms. A crimped or compressed implant 2 is shown in the delivery platform 8. In a similar manner, the implants positioned on the delivery platforms 8 can be identical or substantially identical, though in other embodiments of the disclosure the implants 2 can be different sizes and constructions.

As can be seen in FIG. 2, the one or more delivery platforms 8 can be disposed on the inner shaft 26 adjacent the distal end portion 4 of the delivery catheter 1. Each of the delivery platforms 8 can comprise a recess positioned between a pair of annular pusher bands 27. In the illustrated embodiment of the disclosure, a proximal annular pusher band 27A of a first platform 8A is also the distal annular pusher band 27A of the platform 8B located immediately proximal. The annular pusher bands 27 have a larger outer diameter as compared to the delivery platforms 8 at the recesses. In some embodiments of the disclosure, the recesses can be defined as the smaller diameter region next to, or between, one or two annular pusher bands 27 and/or an additional feature on the inner shaft 26. In a modified arrangement of the delivery catheter, the recesses could be eliminated by providing another structure for axially fixing the implants 2 along the inner shaft 26 (such as, for example, a peg or interlock that engages a respective implant 2).

One or more of the annular pusher bands 27 can also function as radiopaque marker bands. For example, proximal and distal radiopaque marker bands can be provided to make the ends of a respective platform 8 visible using standard angiographic or other visualization techniques and thus indicate to the user the location of the implants 2 on the delivery catheter 1. The annular pusher bands 27 can take any suitable form, for example including one more of tantalum, iridium, and platinum materials. In some embodiments of the disclosure, the pusher bands 27 can be about 4 mm long with about 12 mm recesses between them. In such embodiments of the disclosure, an implant having an axial length (e.g., in a crimped configuration) of between 4-15 mm (e.g., 4-12 mm, 8-12 mm, between 4-9 mm, between 10-11 mm, overlapping ranges thereof, or any value within the recited ranges, including 4.5 mm, 5.0 mm, 5.5 mm, 6.0 mm, 6.5 mm, 7.0 mm, 7.5 mm, 8.0 mm, 8.5 mm, 10.3 mm, 10.5 mm, 11 mm, 11.5 mm, 12 mm) can be positioned between the pusher bands 27. In some implementations, the pusher bands 27 can be between 50-70% of the size of the recess and/or the implant. In some implementations, the pusher bands 27 are about 60% of the size of the recess and/or the implant. In other implementations, the pusher bands 27 can be much smaller, at between 10-20% of the size of the recess and/or the implant. This may be the case especially with longer implants. In some implementations, at least the proximal ends of the pusher bands 27 can have a radius to help reduce potential for catching on deployed implants during retraction of the delivery catheter 1. The pusher bands 27 may range from between 10% and 75% (e.g., between 10% and 20%, between 10% and 30%, between 15% and 30%, between 10% and 50%, between 20% and 50%, between 25% and 75%, between 30% and 60%, between 10% and 40%) of the size of the recess and/or the implant.

Reducing the difference in length between the recess and the implant can increase the precision of placement of the implant, especially with implants having only one, two, three, or four columns of cells. A column of cells can be defined as a pair or rings and each ring can be formed by series of struts and apexes that can form a repeating pattern in certain embodiments of the disclosure. In such embodiments, implants with one, two, three, or four columns of cells can be formed by two, three, four or five rings respectively. In some embodiments of the disclosure, the recess can be less than 1, 0.5, 0.4, 0.3, 0.25, or 0.2 mm longer than the implant. The implant can be any number of different sizes, such as 4, 5, 6, 6.5, 8, 10, or 12 mm in axial length.

Figure 3A:
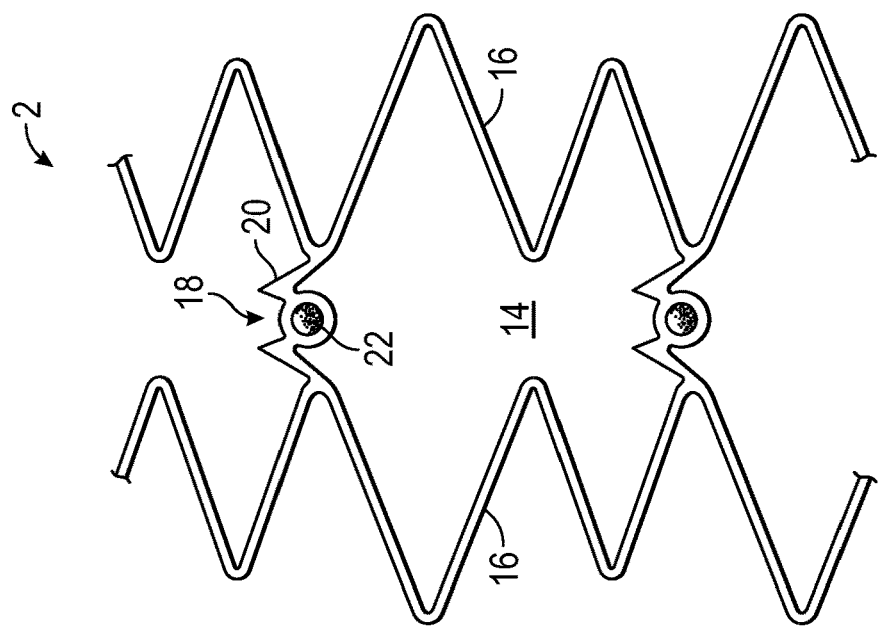
FIG. 3A is a close-up view of a portion of the implant of FIG. 3 in an unconstrained, or uncompressed, state.
Figure 3:
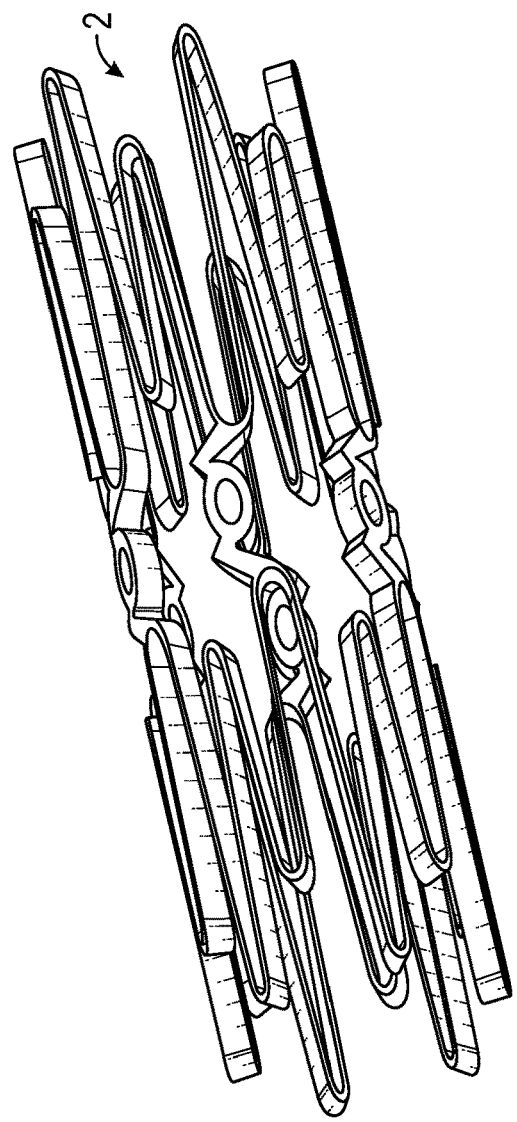
FIG. 3 illustrates one example of an intravascular implant that may be delivered using the delivery device of FIG. 1. The intravascular implant is shown in a crimped, or compressed, state.

FIGS. 3 AND 3A illustrate one example embodiment of an implant 2 that can be delivered by the delivery device 1. Relatively small intraluminal devices, for example with only one column (as shown in FIGS. 3 & 3A), two or three columns of cells, can be delivered at precise treatment locations and spaced appropriately to not overlap. FIG. 3A shows a flattened section of the implant (e.g., intravascular, or endovascular, implant) of FIG. 3. It can be seen that a single column of cells 14 are formed by two concentric rings of undulating struts 16 connected by bridge members 18. In the illustrated embodiment, the bridge members 18 have a pair of anchors 20 and a radiopaque marker 22. However, other embodiments of implants do not include anchors. Multiple small endovascular implants can be used to treat a single or multiple lesions. This can minimize the amount of foreign material in the body, while providing needed holding forces. Various embodiments of implants are described in more detail in Applicants' related applications (e.g., U.S. patent application Ser. No. 13/179,458 filed Jul. 8, 2011, published as US 2012/0035705 (IVAS.002P4); U.S. patent application Ser. No. 13/749,643 filed Jan. 24, 2013, published as US 2013/0144375 (IVAS.002P6); U.S. Provisional Application No. 62/901,193 filed Sep. 16, 2019 (IVAS.038PR2) and PCT Application No. PCT/US2020/029351 filed Apr. 22, 2020, published as WO 2020/219567 (IVAS.038WO); the contents of each of which are incorporated by reference herein and made a part of this specification).

Each radiopaque marker can be press-fit or swaged into a circular eyelet on the respective bridge member of the intraluminal device. Swaging is a forging process in which the dimensions of an item are altered using dies into which the item is forced. Swaging is usually a cold working process; however, it is sometimes done as a hot working process. Swaging is normally the method of choice for precious metals since there is no loss of material in the process. The radiopaque markers discussed herein with respect to the intraluminal devices and delivery devices can be any number of different materials, including gold, platinum and tantalum.

In some configurations, the outer sheath 12 can be constructed as a laminate of polymer extrusions and braided wires embedded in the polymer extrusions. Flexibility and stiffness can be controlled through the number of braid wires, the braid pattern and pitch of the braid. In one implementation, the outer sheath 12 can be made of polyether block amide (PEBA), a thermoplastic elastomer (TPE) available under the trade name PEBAX.

In some configurations, the outer sheath 12 has a thinner inner liner made of a polytetrafluoroethylene (PTFE), such as TEFLON, or PEEK material. Any radiopaque marker band(s) 28 or other radiopaque material may be positioned between these two layers. In other embodiments of the disclosure, the radiopaque marker band(s) 28, or other radiopaque material can be embedded within one or more layers of the outer sheath 12. The radiopaque marker band(s) 28 can range from 0.5 mm to 5 mm wide and be located from 0.5 mm to 10 mm proximal from the distal terminus of the outer sheath 12. In some embodiments of the disclosure, the radiopaque marker band(s) 28 can be 1 mm wide and 6 mm proximal from the distal terminus of the outer sheath 12.

In some implementations, the catheter assembly 11 includes an outer support shaft comprised of PEEK or other extruded flexible polymer and is configured to provide support for the smaller diameter outer sheath 12, thereby forming a tri-axial catheter assembly. In some implementations, the outer support shaft and the inner shaft 26 are fixed in position at the proximal end of the deployment handle 10 and the outer sheath 12 translates coaxially over the inner shaft 26 and inside the outer support shaft. The outer sheath 12 may taper in diameter from the proximal end to the distal end. The tapering may be uniform along the entire length or may have constant-diameter portions that each taper along the length.

In other embodiments of the disclosure, the outer sheath 12 is formed of a hypotube, such as a metal or plastic hypotube. Flexibility and stiffness of a hypotube outer sheath 12 can be controlled by many features such as the slope and frequency of a spiral cut along the length of the hypotube. The slope and frequency may be uniform or may vary along the length of the hypotube. Different portions of the length of the hypotube may be designed to be more flexible than others.

The delivery device 1 can be used, for example, as part of a procedure to treat atherosclerotic occlusive disease. The delivery device 1 can be used to deliver one or more implants which can also be referred to herein as an intravascular implant, such as a stent, to a site of plaque accumulation. The intravascular implant(s) can stabilize the site and/or hold pieces of plaque out of the way of blood flow. The delivery device 1 is described with respect to delivery of self-expandable intravascular implants, such as those shown in FIGS. 1-3A. It will be understood that although the implants and methods described herein are described primarily with reference to vascular procedures (e.g., above-the-knee or below-the-knee angioplasty procedures) and intravascular implants, certain features and aspects of the embodiments disclosed herein can also find utility used in treatments for other parts of the body (e.g., other body lumens, passages, spaces, cavities) and/or for delivery of other types of implants or medical devices (e.g., staples, plugs, sutures, grafts, anchors). In some implementations, the delivery device may be introduced via other routes of delivery and not just intravascular (e.g., percutaneous, laparoscopic, endoscopic, open surgical approaches).

C. Deployment Handle

1. Overview

Figure 4:
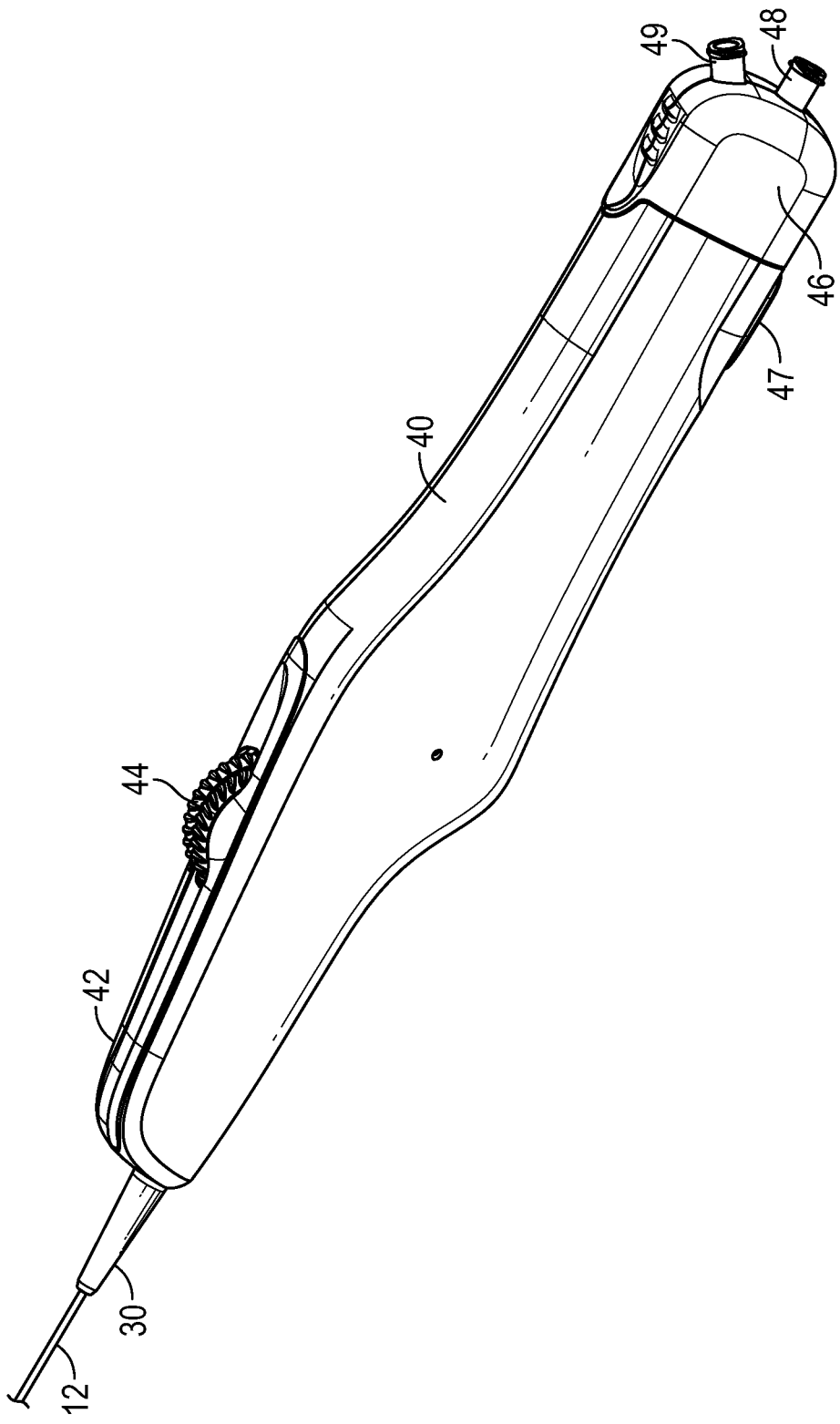
FIG. 4 is a perspective view of a rotary deployment handle of the delivery device of FIG. 1.

FIG. 4 is a close-up perspective view of the rotary deployment handle 10 at the proximal end portion 6 of the delivery device of FIG. 1. FIG. 4 illustrates external components of the deployment handle 10 that are visible to the operator. In the illustrated embodiment, the external components of the handle 10 include a main body housing 40, a lockout lever 42, a thumbwheel 44, a re-sheath housing 46, a re-sheath button 47, and flush ports 48, 49. The main body housing 40 may be ergonomically shaped to as to facilitate holding by a single hand of the operator. The lockout lever 42 extends into an upper opening of the main body housing 40 and forms an upper proximal surface of the handle 10. The lockout lever 42 can be a component of the lockout assembly configured to prevent inadvertent deployment of any of the implants until an operator intentionally disables the lockout mechanism, which may be performed by a single step or operation performed by the operator. The structural components and functionality of the lockout mechanism will be described later in more detail. The thumbwheel 44 extends out of the upper surface of the lockout lever 42. In accordance with several embodiments of the disclosure, the lockout lever 42 physically hides the thumbwheel 44 when the lockout lever 42 is in a raised position, thereby indicating to a user, or operator, that the lockout lever 42 must be pressed inward (e.g., down) in order to utilize the delivery device 1. The lockout lever 42 may include printed arrows or other indicia indicating to the operator to press inward (e.g., down) on the lockout lever 42 to initiate use. The thumbwheel 44 is a component of the deployment mechanism configured to retract the outer sheath 12 to facilitate deployment of the implants 2. The re-sheath housing 46 is removably coupled to a proximal end of the main body housing 40 and facilitates re-sheathing by retracting the inner shaft 26 within the outer sheath 12 when the operator desires to move the delivery device 1 to another location after deployment of one or more of the implants. The re-sheath button 47 extends out of a bottom surface of the main body housing 40 and enables/disables the re-sheathing functionality, as well as unsheathing after re-sheathing. The re-sheathing structural components and functionality will be described later in more detail. The flush ports 48, 49 extend out of a proximal surface of the re-sheath housing 46. The flush ports 48, 49 are ports of a proximal luer hub 50 (shown in FIG. 5) that facilitates flushing of the various lumens and spaces within the delivery device 1 prior to use, as will also be described later in more detail.

Figure 5:
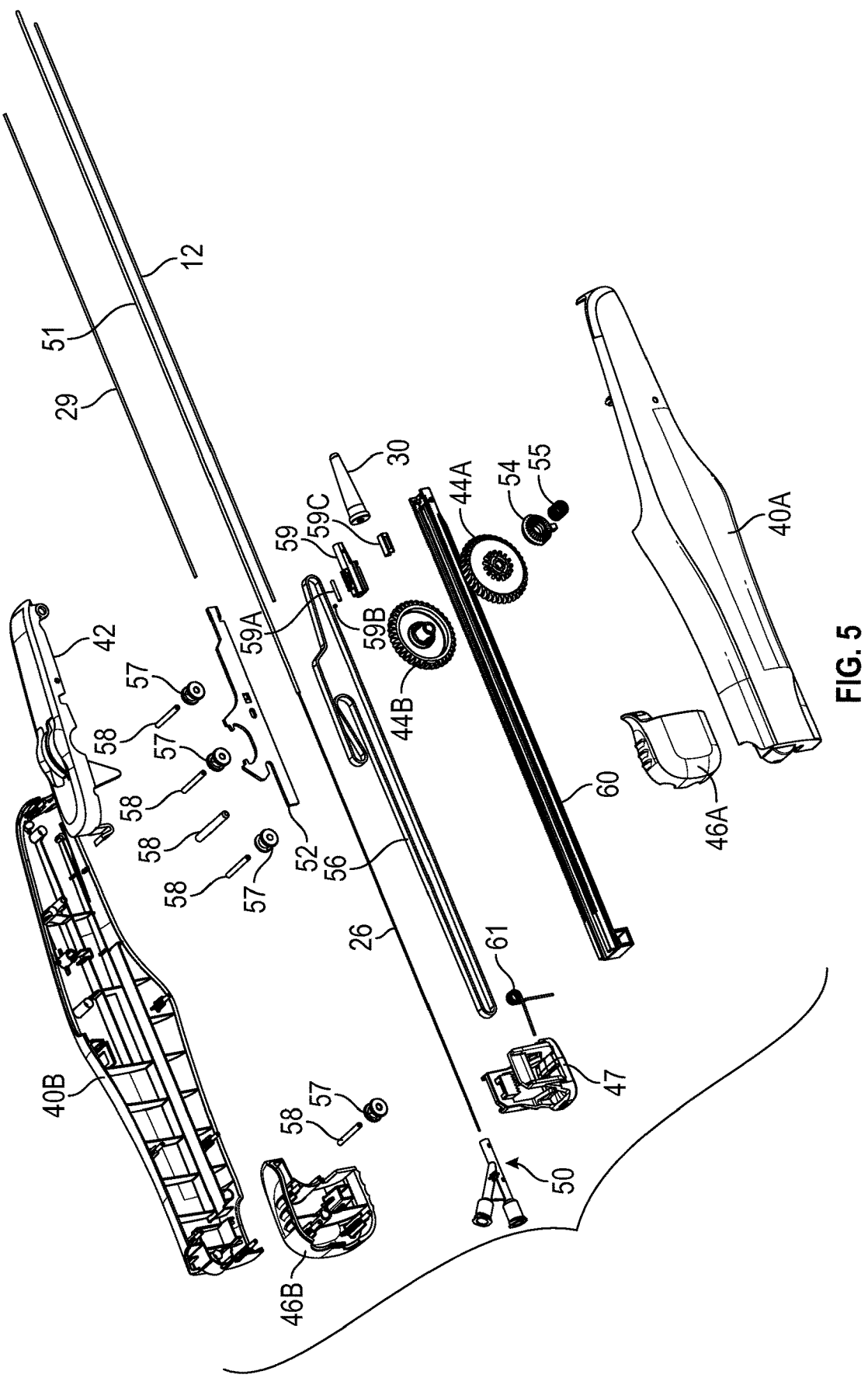
FIG. 5 illustrates an exploded assembly view of several components of the rotary deployment handle of FIG. 4.

FIG. 5 illustrates an exploded assembly view of several components of an embodiment of the rotary deployment handle 10. As shown in FIG. 5, the main body housing 40 of FIG. 4 may comprise a two-part housing: a right side housing portion 40A and a left side housing portion 40B. The re-sheath housing 46 may also comprise a two-part housing: a right side re-sheath housing 46A and a left side re-sheath housing 46B. The two parts of the main body housing 40 and the re-sheath housing 46 may be configured to be snap fit together during assembly via various corresponding mating members. The inner shaft 26 is configured to be received within a distal opening of the proximal luer hub 50. A delivery tube 51 surrounds the inner shaft 26 in a coaxial manner. The delivery tube 51 may comprise stainless steel or other biocompatible polymeric and/or metallic material in some implementations. A lockout assembly of the illustrated handle 10 includes the lockout lever 42 and a lockout plate 52.

As further shown in FIG. 5, the thumbwheel 44 also includes two parts: a right thumbwheel 44A and a left thumbwheel 44B. The deployment mechanism of the deployment handle 10 further includes a ratchet wheel 54, a ratchet spring 55, a retraction belt 56, multiple pulleys 57, multiple axels 58, and a belt link, or shuttle 59. The shuttle 59 interfaces or interacts with multiple components, including an outer sheath sleeve 59A, an O-ring 59B, and a shuttle clip 59C. FIG. 5 also illustrates two additional components of the re-sheath mechanism: a re-sheath rack 60 and a re-sheath button spring 61 that is configured to bias the re-sheath button 47 into a default resting position in which re-sheathing cannot be performed, or is prevented.

Figure 6:
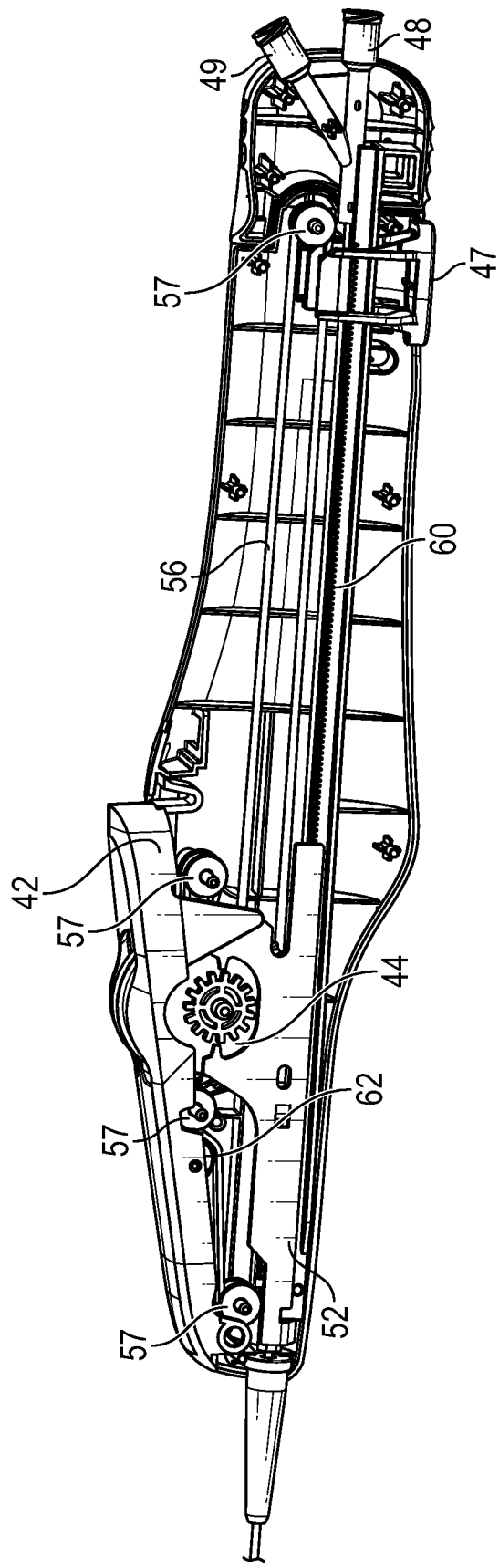
FIG. 6 is a side view of the rotary deployment handle of FIG. 4 with the left side housing portion removed.

FIG. 6 is a side view of the rotary deployment handle 10 with the left side housing portion 40B removed and shows several of the internal components of the rotary deployment handle 10 when assembled. FIG. 6 illustrates the thumbwheel 44, the lockout lever 42 and the lockout plate 52 of the lockout assembly/mechanism, the retraction belt 56, the belt pulleys 57, the re-sheath rack 60 and the re-sheath button 47 of the re-sheath mechanism, and the flush ports 48, 49 of the proximal luer hub 50.

FIG. 6 also shows a tensioner pulley 62 positioned underneath the lockout lever 42. As shown in FIG. 6, the lockout lever 42 is initially provided in a locked configuration in which the proximal end of the lockout lever 42 protrudes out of the upper surface of the main body housing 40. When the proximal end of the lockout lever 42 is pressed down into the main body housing 40 by the operator, the tensioner pulley 62 is moved down as well, engaging an upper surface of the retraction belt 56 to properly tension the retraction belt 56 to facilitate efficient operation and rotation of the retraction belt 56 when actuated. The pressing down of the proximal end of the lockout lever 42 also disengages the thumbwheel lockout mechanism, thereby allowing the thumbwheel 44 to rotate, as will be described in more detail in connection with FIGS. 7A-7D. The retraction belt 56 wraps around the belt pulleys 57 as shown. To start retracting the outer sheath 12, the operator slowly rotates the thumbwheel 44 in the proximal direction (clockwise rotation), thereby causing linear displacement of the shuttle 59 and the outer sheath 12 (which is bonded to the shuttle 59) relative to the inner core assembly 13 loaded with the implants 2, which in turn, results in deployment of the implants 2. An inner barrel of one of the thumbwheels 44A, 44B may include barrel teeth that are sized to correspond with teeth along the retraction belt 56. As the thumbwheel 44 is rotated, the operator will experience tactile feedback and hear distinct audible clicks. The audible clicks may provide the operator with a qualitative assessment of a rate (or speed) at which unsheathing is occurring so as to allow the operator to adjust the rate. Both the right thumbwheel 44A and left thumbwheel 44B are linked to each other and move together such that only one of the them needs to be rotated by the operator. The thumbwheels 44A, 44B include gripping features (e.g., ridges and grooves) on their outer surfaces to facilitate ease of rotation by a thumb or finger of the operator. The gripping features (e.g., ridges/grooves/texture) may exhibit a slight directionality in order to prompt the operator to rotate the thumbwheel 44 in the proper direction (e.g., clockwise, or toward the operator). In other implementations, the thumbwheel 44 may not include two separate thumbwheel parts and may comprise a single, unitary thumbwheel.

The re-sheath button 47 includes teeth that engage with corresponding grooves in the re-sheath rack 60 when the re-sheath button 47 is in a default un-pressed configuration. When the re-sheath button 47 is pressed inward (e.g., upward), then the teeth of the re-sheath button 47 disengage from the re-sheath rack 60, thereby allowing for proximal and distal movement of the re-sheath rack 60. Following one or more implant deployments, the operator can re-sheath the distal end portion 4 of the catheter assembly 11 by pressing on the re-sheath button 47 with one hand and retracting the re-sheath housing 46 away from the main body housing 40. This motion retracts the re-sheath rack 50 proximally (along with the re-sheath housing 46 and the proximal luer hub 50, which is bonded to the inner core assembly 13). Therefore, since the inner shaft 26 is being pulled back (i.e., proximally), the distal end portion of the inner core assembly 13 is being covered (or re-sheathed) by the previously-pulled back outer sheath 12.

Once the delivery device 1 has been removed from the treatment site (or entirely from the body of the subject), the operator has the option to re-insert and advance the delivery device 1 to another treatment site if there are implants 2 remaining in the delivery device 1. To perform this operation, the operator can guide the delivery device 1 to the appropriate treatment site, press on the re-sheath button 47 with one hand and push on the re-sheath housing 46 with the other hand until the re-sheath housing 46 clicks back in place (e.g., the re-sheath housing 46 re-engages and is flush with the main body housing). This operation un-sheathes the inner core assembly 13 to the same spot where it was last left off before the inner core assembly 13 was re-sheathed, and standard thumbwheel operation may be resumed to effect deployment of one or more remaining implants 2.

2. Lockout Mechanism

Figure 7A:
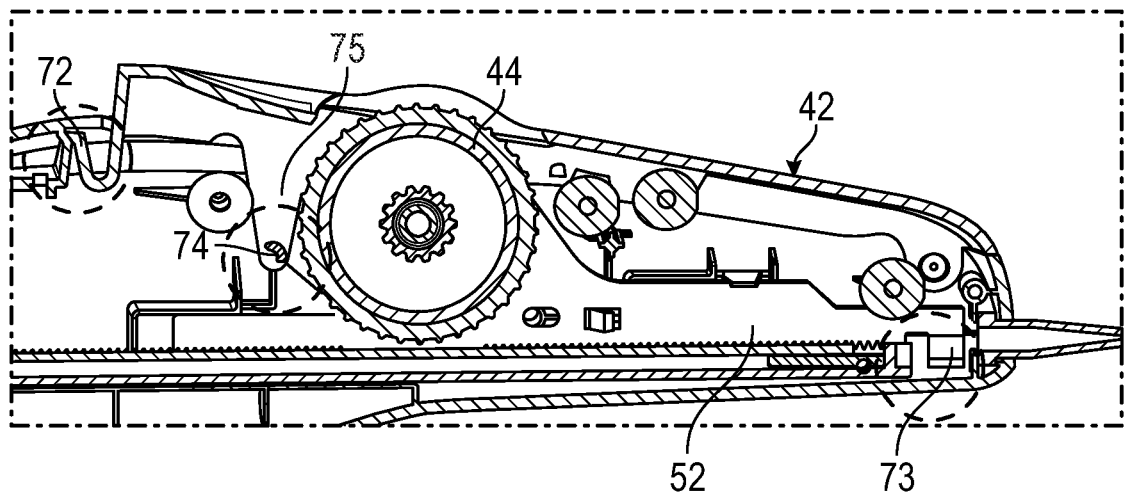
FIGS. 7A-7D illustrate various configurations of the rotary deployment handle of FIG. 4.
Figure 7B:
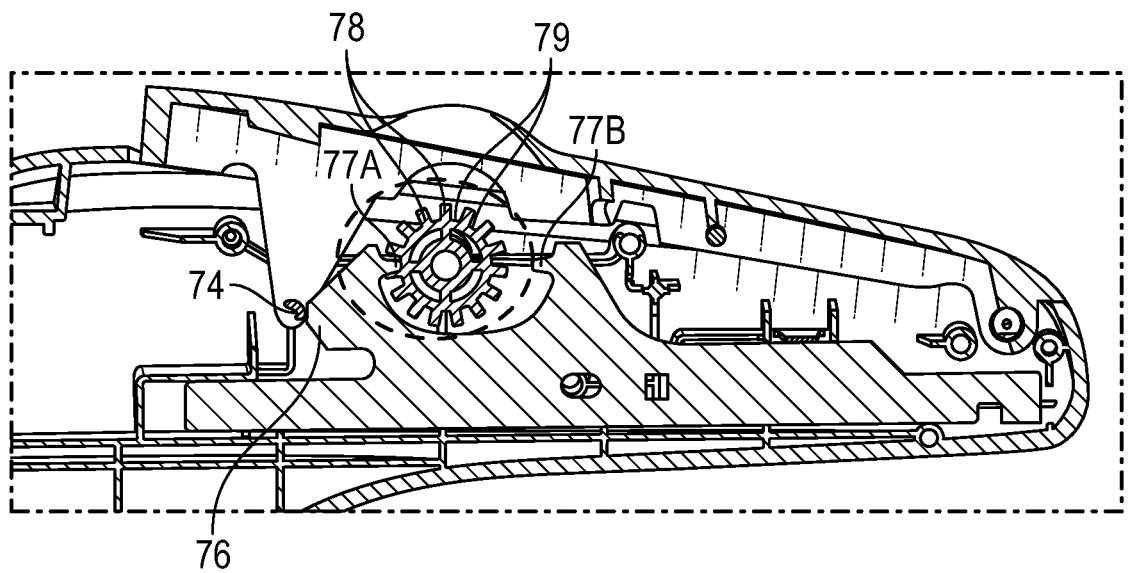

FIGS. 7A-7D help to illustrate the structural components and functionality of the lockout mechanism of the rotary deployment handle 10. FIGS. 7A and 7B illustrate side views of various internal components when the thumbwheel 44 is in a locked configuration. The locked configuration may be the default configuration upon assembly and may be the configuration in which the delivery device 1 is shipped to consumers after manufacture. The initial locked configuration advantageously prevents inadvertent deployment of implants from manufacture until the appropriate time when the operator desires the implants to be deployed at a target treatment site or location. The initial locked configuration may be referred to as the shelf lock feature, meaning, for example, that the device 1 is locked as it sits on the shelf prior to use.

As shown in FIGS. 7A and 7B, the proximal end portion of the lockout lever 42 is raised higher than (e.g., is not flush with) the upper surface of the main body housing 40 of the handle 10. The proximal end of the lockout lever 42 includes a hook 72 that is resting against a bottom edge of the upper surface of the main body housing 40 in the locked configuration. The lockout plate 52 is biased to be pushed in a proximal direction by a torsion spring or other biasing member (not shown) that links the left side housing portion 40B to the lockout plate 52. In the locked configuration, a boss, or nub, 74 disposed on a triangular extension 75 extending downward from a lower edge of the proximal end portion of the lockout lever 42 abuts against a proximal-most edge of an upper portion 76 of the proximal end portion of the lockout plate 52, thereby preventing the lockout plate 52 from moving proximally based on the bias of the torsion spring. A gap is shown in FIG. 7A between the distal end portion 73 of the lockout plate 52 and the distal terminus of the re-sheath rack 60. As shown in FIG. 7B, when in the locked configuration/position, a proximal engagement member 77A of the lockout plate 52 engages with a recess 79 between respective teeth 78 of an inner gear of the thumbwheel 44 to "lock out", or prevent, the thumbwheel 44 from rotating.

Figure 7C:
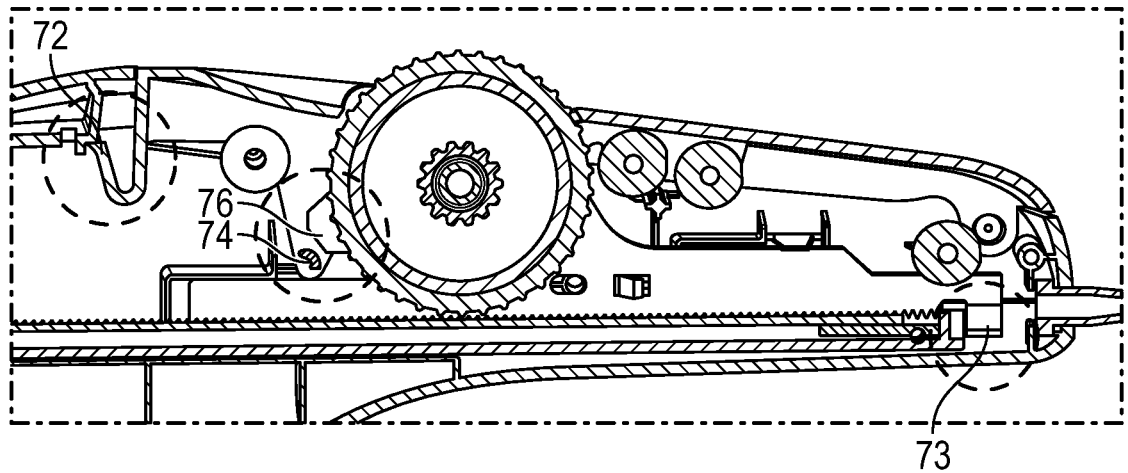
Figure 7D:
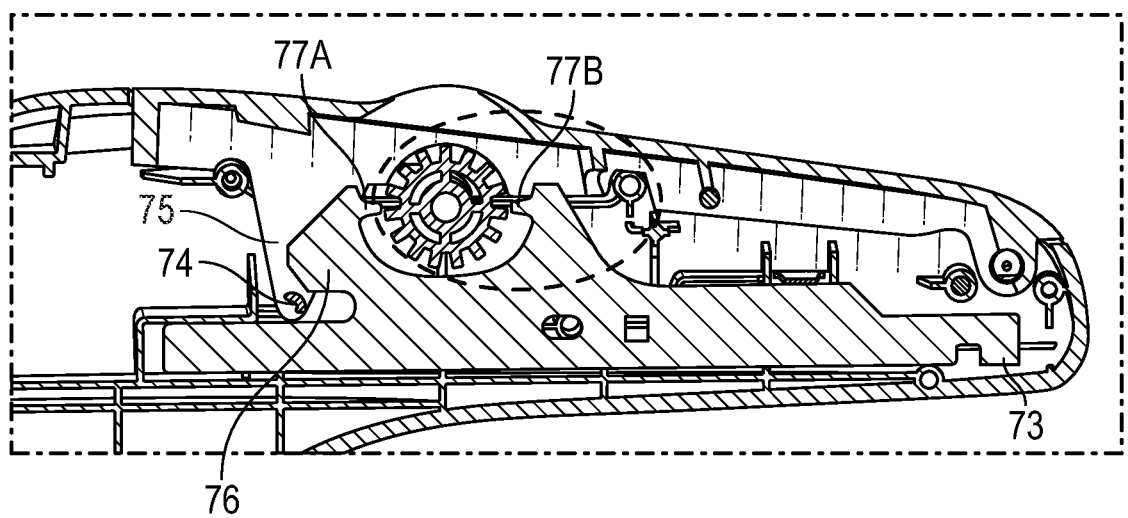

FIGS. 7C and 7D illustrate side views of various internal components when the thumbwheel 44 is in an unlocked configuration after the proximal end portion of the lockout lever 42 has been pressed downward by the operator. As shown in FIG. 7C, in the unlocked configuration, the hook 72 is shown in a lower position within the main body housing 40 than in FIG. 7A and is hooked into a detent of the housing 40. When the proximal end portion of the lockout lever 42 is pressed downward, the boss or nub 74 on the triangular extension 75 of the lockout lever 42 no longer abuts against the proximal-most edge of the upper portion 76 of the proximal end portion of the lockout plate 52, thereby allowing the lockout plate 52 to move toward the proximal direction as a result of a bias force (e.g., the torsion spring bias). As shown in FIG. 7C, no gap exists between the distal end portion 73 of the lockout plate 52 and the distal terminus of the re-sheath rack 60. As shown in FIG. 7D, because the lockout plate 52 has moved proximally, the proximal engagement member 77A is no longer engaged with the gear teeth 78 or recesses 79 of the thumbwheel 44. Accordingly, the thumbwheel 44 is free to rotate in this unlocked, or neutral, configuration. As shown in FIG. 7D, the lockout plate 52 does not move proximally enough that the distal engagement member 77B engages with the gear teeth 78 or recesses 79 of the thumbwheel 44. The engagement members 77 may also be referred to as heads of the lockout plate 52.

3. Ratchet Wheel and Thumbwheel Mechanism

Figure 8A:
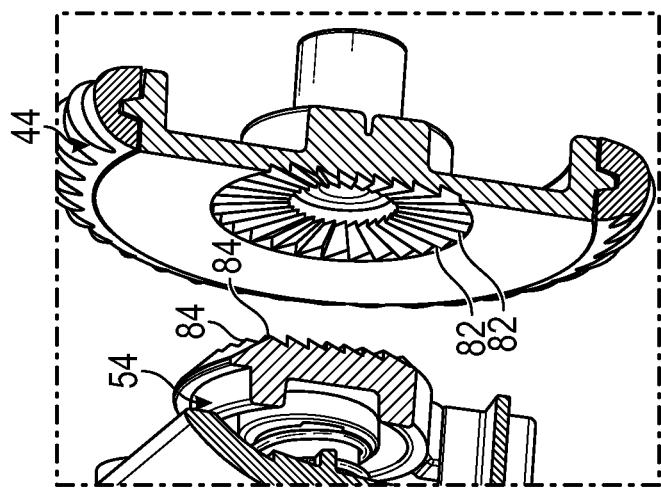
FIG. 8A is a close-up exploded view illustrating the interaction of a ratchet wheel and the thumbwheel of the rotary deployment handle.
Figure 8:
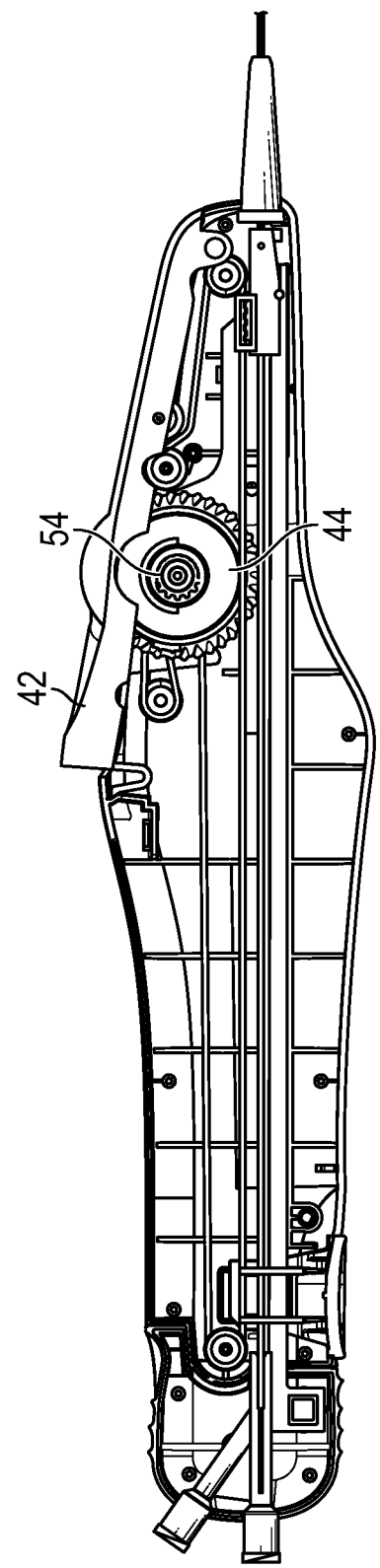
FIG. 8 is a right side view showing various internal components of the rotary deployment handle of FIG. 4 with the right side housing portion removed.

Turning to FIGS. 8 AND 8A, an embodiment of a mechanism to prevent rotation of the thumbwheel 44 (and therefore retraction belt 56) in a reverse direction (e.g., counterclockwise direction) is illustrated and described. This mechanism advantageously prevents against inadvertent deployment of implants and/or damage to the implants or body tissue (e.g., vessel wall). FIG. 8 is a right side view showing various internal components of the rotary deployment handle 10 with the right side housing portion 40A removed. FIG. 8A is a close-up exploded view illustrating the interaction of the ratchet wheel 54 and the thumbwheel 44 of the rotary deployment handle 10. The outer, or right, side of the right thumbwheel 44A includes a circular area of teeth 82 that engage with corresponding teeth 84 on an inner, or left, side of the ratchet wheel 54. The ratchet wheel 54 may be mounted on a boss of the right side housing portion 40A (not shown) and the ratchet spring 55 (shown in FIG. 5).

When the thumbwheel 40 is rotated, or scrolled, in a "normal" clockwise direction (i.e., towards the operator, towards the proximal end of the handle), the thumbwheel rotation causes the ratchet spring 55 to compress and enables the thumbwheel teeth 82 to ride over the teeth 84 of the ratchet wheel 54. This riding over of the teeth 84 of the ratchet wheel 54 creates a "ratcheting", or "clicking" sound with a defined movement of the thumbwheel 54, thereby advantageously providing the operator with tactile and/or audible feedback, as well as slowing down the rotation to ensure more accurate results when deploying the implants and reducing the likelihood of accidental implant deployment.

When the thumbwheel 44 is attempted to be rotated, or scrolled, in the reverse direction (i.e., away from the operator, towards the distal end of the handle), an angle of the teeth 82 of the thumbwheel and an angle of the teeth 84 of the ratchet wheel 54 are designed in a manner to prevent rotational movement of the thumbwheel 44 in the reverse direction. In accordance with several embodiments of the disclosure, this reverse scrolling prevention feature advantageously prevents, or reduces the likelihood of, re-capture of a partially-deployed implant, which can damage the implant or otherwise affect its proper functionality.

4. Re-sheath Mechanism

Figure 9:
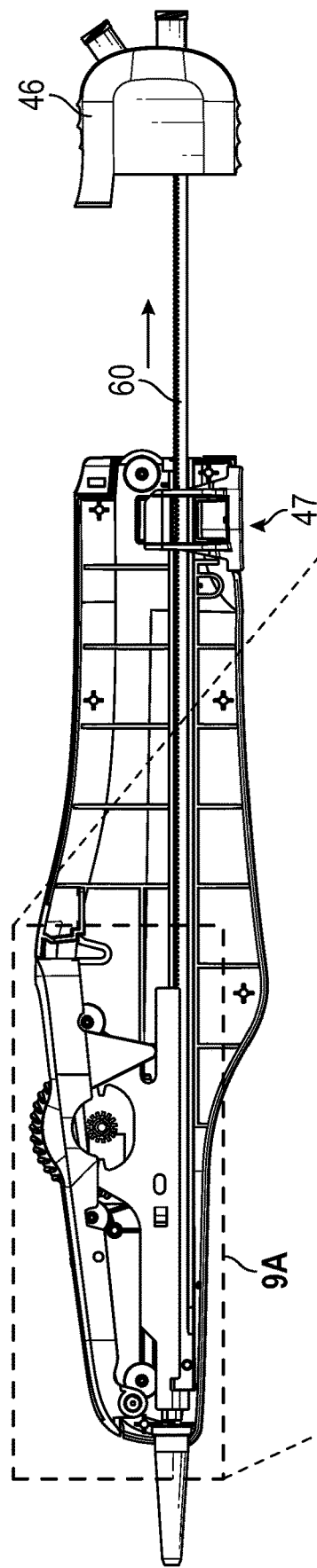
FIG. 9 is a left side view of the rotary deployment handle of FIG. 4 with the left side housing removed.
Figure 9A:
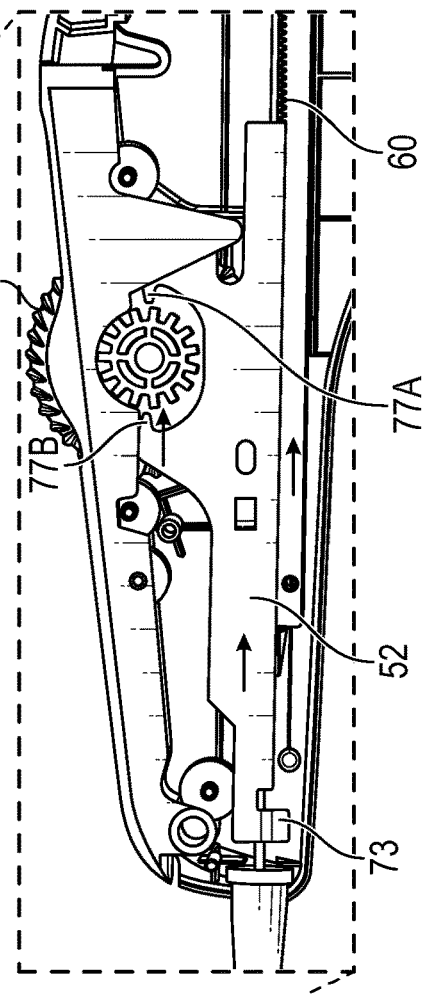
FIG. 9A is a close-up view of a portion of FIG. 9.

FIGS. 9 AND 9A help to illustrate the structural components and functionality of the re-sheath mechanism of the deployment handle 10. FIG. 9 is a left side view of the rotary deployment handle of FIG. 4 with the left side housing portion 40B removed. FIG. 9A is a close-up view of the distal portion of the handle 10 as a re-sheathing function is being initiated. As described previously, to re-sheath the inner core assembly 13, the operator can press the re-sheath button 47 inward and hold the re-sheath button 47 in place, thereby overcoming the bias of the re-sheath spring 61 and disengaging the teeth of the re-sheath button 47 from the corresponding grooves of the re-sheath rack 60. With the re-sheath button 47 pressed, the re-sheath rack 60 can be moved proximally by pulling the re-sheath housing 46 (which may also be referred to as the re-sheath handle) proximally (i.e., toward the operator). The re-sheath button 47 may be pressed with a finger (e.g., thumb) of one hand while the re-sheath housing 46 is manually pulled back, or retracted toward the operator with the other hand (e.g., with a thumb and index finger of the other hand). The re-sheath housing 46 may be pulled until a hard stop is felt by the operator. The inner core assembly 13 (including, for example, the delivery tube 51 and the inner shaft 26) is bonded to the luer hub 50 (e.g., within a lumen of flush port 48) in the re-sheath housing 46. Accordingly, pulling back on the re-sheath housing 46 causes the portion of the inner core assembly 13 including the inner shaft 26 (with the previously-exposed implant areas) that was previously deployed out of the outer sheath 12 to be pulled back into the distal end portion of the outer sheath 12, thereby re-sheathing the inner core assembly 13 (including the inner shaft 26). The re-sheathing functionality advantageously increases safety and reduces likelihood of injury to body tissue or to the implants when the delivery device 1 is removed from the target treatment site or from the patient's anatomy.

With reference to FIG. 9A, during the re-sheathing process, proximal retraction of the re-sheath housing 46 and re-sheath rack 60 causes the lockout plate 52 to also shift in the proximal direction. Because the distal terminus of the re-sheath rack 60 is no longer abutting against a projection extending from the distal end portion 73 of the lockout plate 52 when the re-sheath rack 60 moves proximally, the proximally-directed bias exerted by the torsion spring or other biasing member operably coupled to the lockout plate 52 causes the lockout plate 52 to move in a proximal direction. The proximal movement of the lockout plate 52 causes the distal engagement member 77B of the lockout plate 52 to be received within a recess between teeth of the gear of the thumbwheel 44, thereby effectively preventing rotation of the thumbwheel 44 during re-sheathing. This lockout mechanism during re-sheathing advantageously reduces the likelihood of accidental implant deployments during re-sheathing and unsheathing after re-sheathing.

In order to re-deploy any additional undeployed implants 2 remaining in the delivery device 1 (e.g., in a different target treatment site of the same patient after clinical review), the operator can again press and hold in the re-sheath button 47 and push the re-sheath housing 46 distally (away from the operator) until the re-sheath housing 46 mates or otherwise couples again with the proximal end of the main body housing 40. Again, because the inner core assembly 13 is bonded to the luer hub 50 (e.g., within a lumen of fluid port 48) within the re-sheath housing 46, movement of the re-sheath housing 46 distally causes the inner core assembly 13 (including the inner shaft 26) to be "un-sheathed" again to the same position, or configuration, it was in (e.g., relative to the distal terminus of the outer sheath 12) prior to the "re-sheathing."

5. Shuttle and Flush Port Operation

Figure 10:
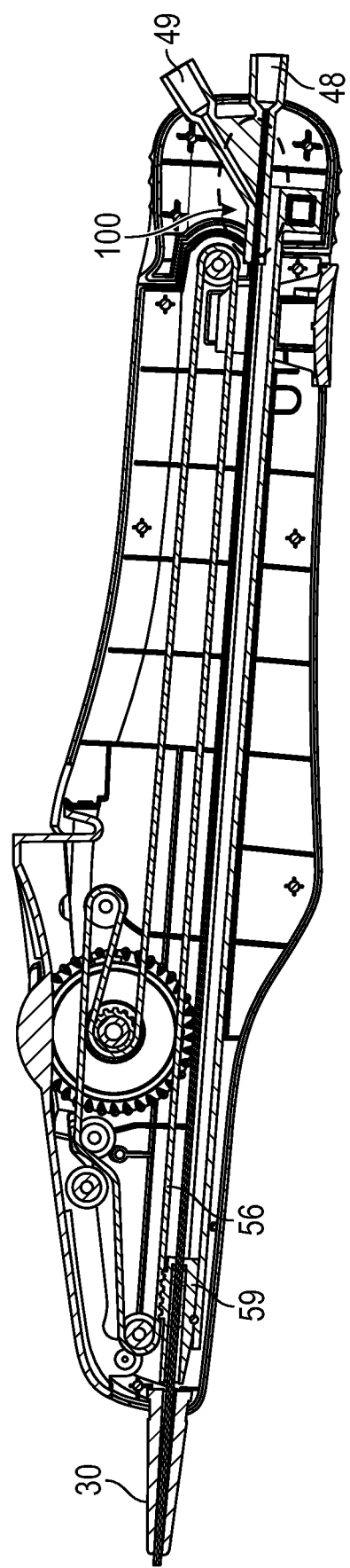
FIG. 10 is a left side view of the rotary deployment handle of FIG. 4 that shows various internal components with the left side housing portion removed.

FIG. 10 is a left side view of the rotary deployment handle 10 that shows various internal components with the left side housing portion 40B removed. FIG. 10 illustrates the shuttle 59 engaged with the retraction belt 56 that is wrapped around the pulleys 57. FIG. 10 also illustrates a side cross-section view of the flush ports 48, 49 of the proximal luer hub 50. The circled portion shows a bond area 100 where the inner catheter assembly 13 (including the inner shaft 26 and the delivery tube 51) is bonded within the proximal luer hub 50 (e.g., within a lumen of flush port 48 and/or a lumen of flush port 49).

Figure 10A:
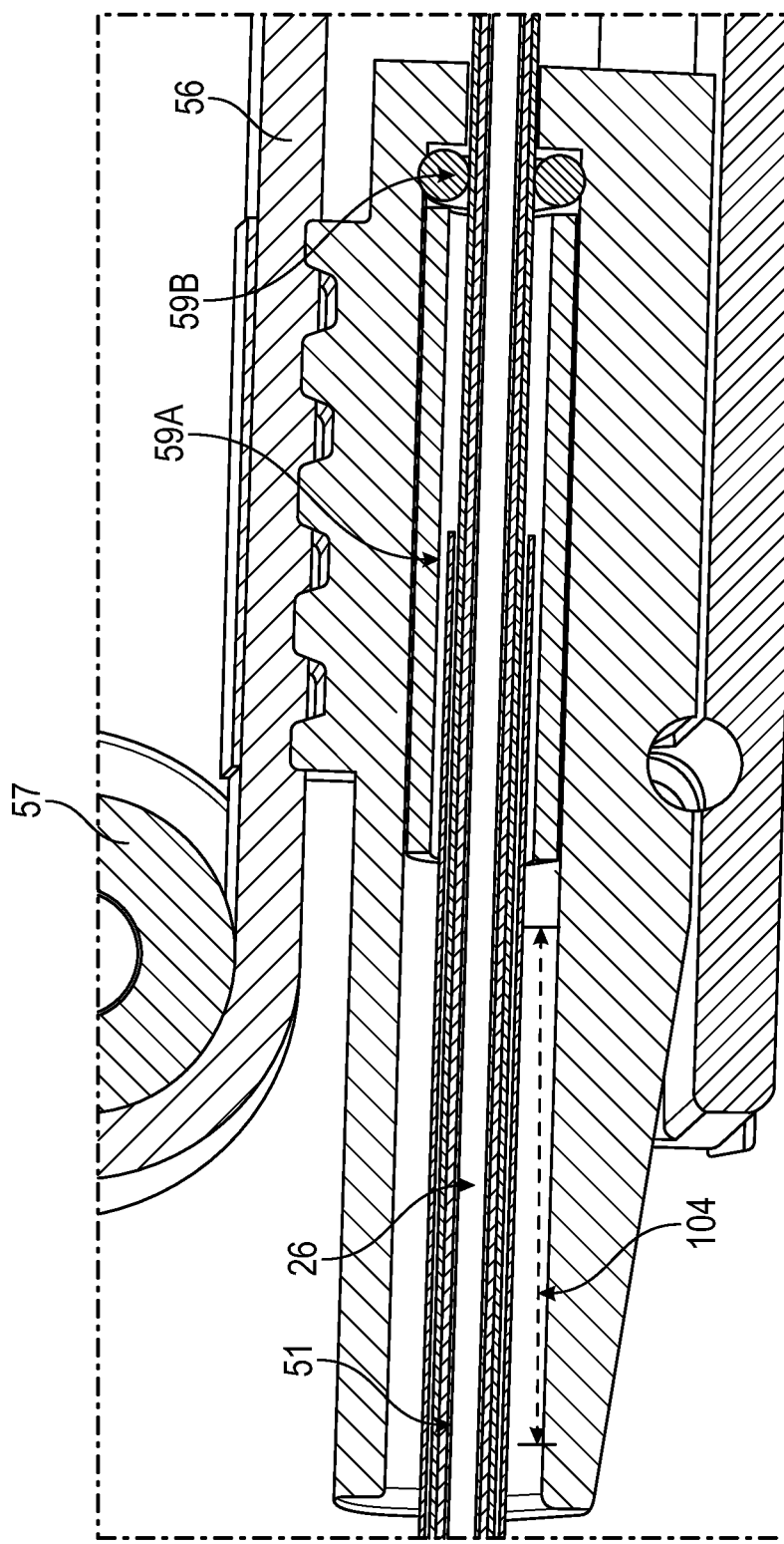
FIG. 10A illustrates a close-up side cross-section view of various internal shuttle components.
Figure 10B:
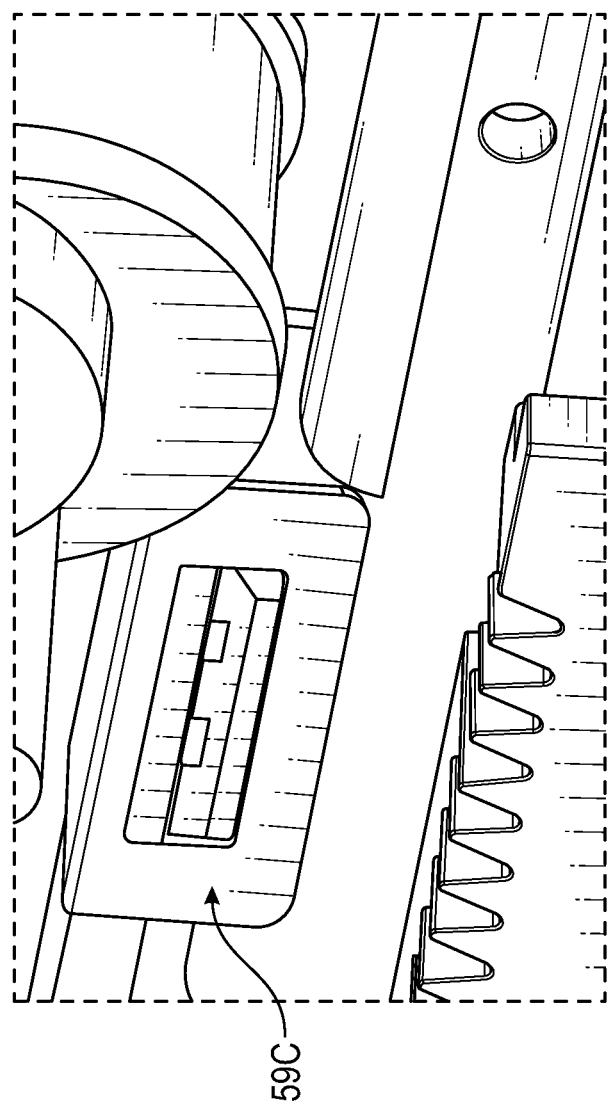
FIG. 10B is a close-up side view of a shuttle clip that facilitates coupling of the belt with the shuttle.

FIG. 10A illustrates a close-up side cross-section view of various internal shuttle components. The shuttle 59 houses the delivery tube 51, the bonding area 104 on the proximal end of the outer sheath 12, the outer sheath sleeve 59A, and the O-ring 59B. The delivery tube 51 protects the inner shaft 26 and creates a fluid pathway between the inner shaft 26 and the inner diameter of the delivery tube 51. The bonding area 104 is a designated area where the outer sheath 12 is bonded to the inside of the shuttle 59 during assembly/manufacture. The O-ring 59B advantageously prevents against, or reduces the likelihood of, backflow of fluid from reaching the internal area of the handle 10 and allows the delivery tube 51 to move (e.g., slide, translate) within the O-ring 59B. The outer sheath sleeve 59A advantageously prevents, or reduces the likelihood of, excess movement of the O-ring 59B and prevents, or reduces the likelihood of, excess glue from the bonding area 104 from reaching the O-ring 59B. With reference to FIG. 10B, on top of the shuttle 59 is where the retraction belt 56 is mated and clipped onto the shuttle 59 via the shuttle clip 59C that snaps onto retention wings of the shuttle 59.

Figure 10C:
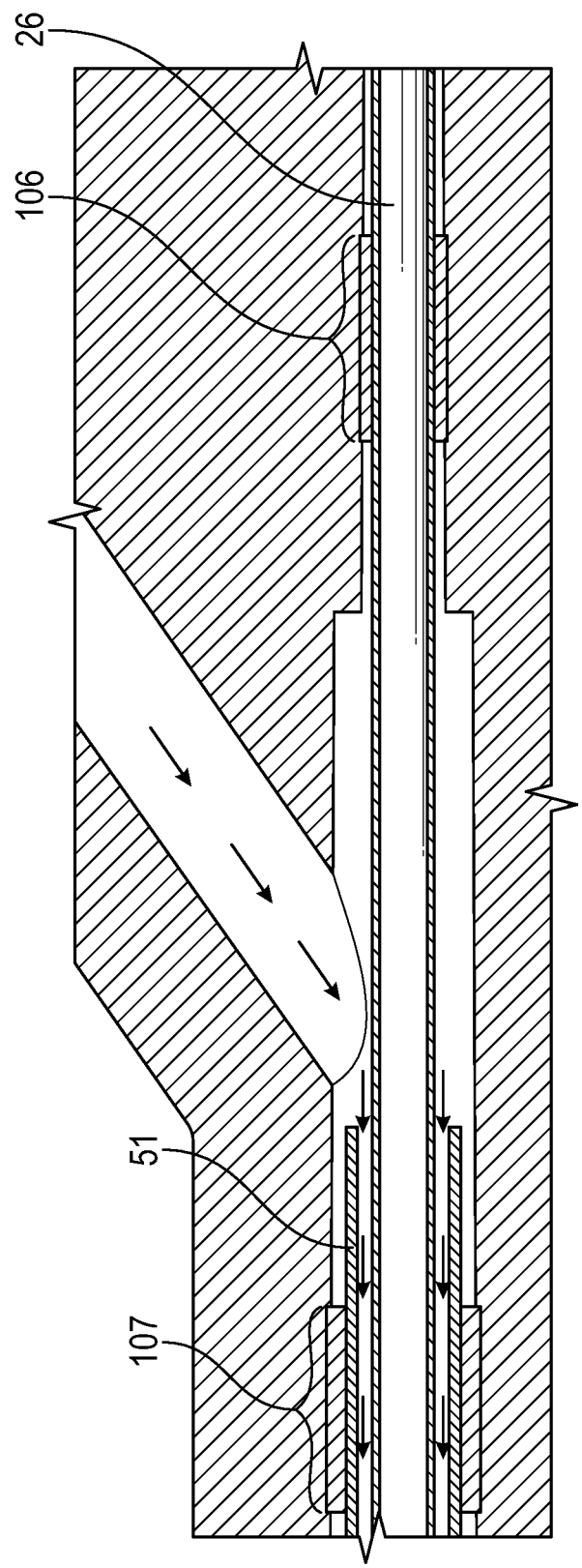
FIG. 10C is a close-up side cross-section view of a flush port of the rotary deployment handle.
Figure 10D:
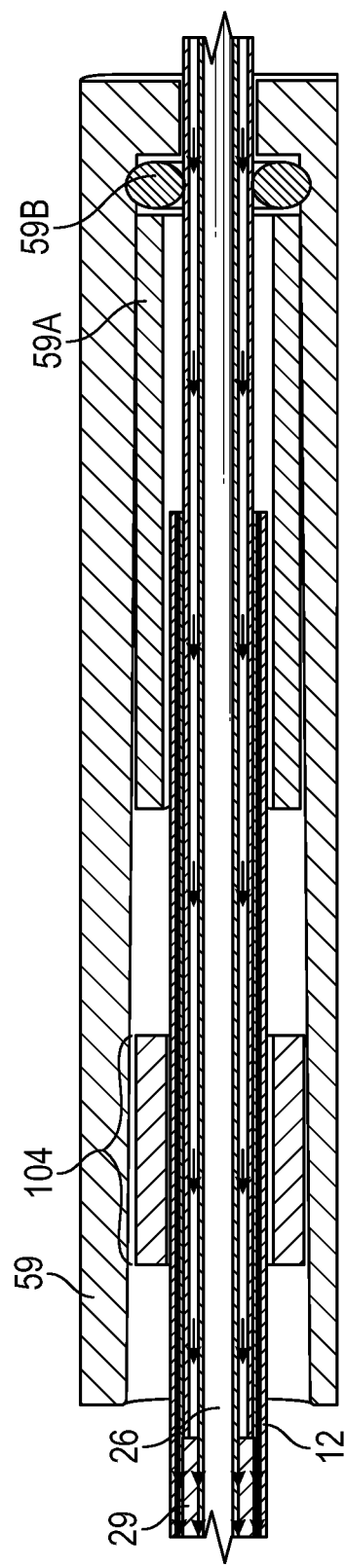
FIGS. 10D and 10E are close-up side cross-section views that illustrate fluid pathways that facilitate fluid flushing of the delivery catheter lumens.
Figure 10E:
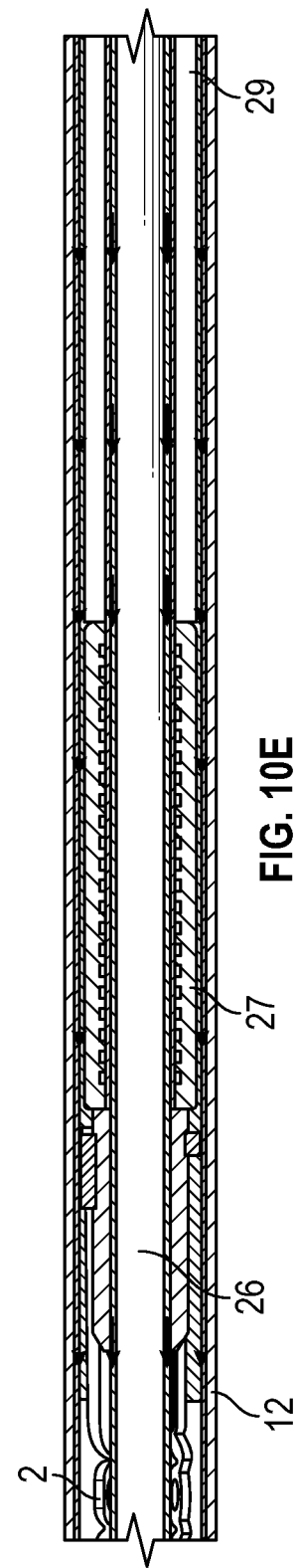

FIG. 10C is a close-up side cross-section view of the flush ports 48, 49 of the rotary deployment handle 10. As described previously, the flush ports 48, 49 advantageously facilitate flushing of the various lumens and spaces of the delivery catheter 1 prior to use to prevent air bubbles and/or increase lubricity. For example, heparinized saline or other fluid flush solution may be introduced through each of the flush ports 48, 49. With reference to FIG. 10C, the fluid pathways (represented by arrows) of the catheter lumen flush begin with the fluid entering through the flush ports 48, 49. As shown by the path of the arrows, the fluid then enters between the inner shaft 26 and the delivery tube 51. FIG. 10C also illustrates a bond area 107 of the delivery tube to the luer hub 50 (e.g., within a lumen of the fluid port 48). Turning to FIG. 10D, the fluid pathways then continue until the distal end of the pusher tube 29 (which in one embodiment, comprises a PEEK tube). Any backflow of fluid between the delivery tube 51 and the outer sheath 12 inside the shuttle 59 comes to a dead-end with the O-ring 59B preventing, or reducing the likelihood of, any fluid ingress into the handle interior. FIG. 10D also illustrates the bond area 104 described in connection with FIG. 10A where the outer sheath 12 is bonded to the inside of the shuttle 59. With reference to FIG. 10E, at the distal end of the pusher tube 59 (or PEEK tubing), the fluid path continues to the distal end of the delivery catheter 1 with the split paths (one path between the pusher tube 29 and the inner shaft 26 and one path between the pusher tube 29 and the outer sheath 12) converging between the outer sheath 12 and the implant areas (e.g., including the pusher bands 27, the implants 2 and bump tubing 28). Accordingly, the construction of the delivery catheter 1 advantageously facilitates fluid flushing from the fluid ports all the way through to the distal end of the delivery catheter 1 without creating internal leaks or significant fluid buildup or stoppage areas.

D. Example Method of Use

FIGS. 11-15 illustrate an example of a method of use of the delivery device 1. For example, implant(s) delivered by the device 1 may be used to treat various conditions such as atherosclerotic occlusive disease. In certain arrangements, the delivery device can be used to deliver one or more implants that can hold loose plaque and/or arterial tissue (dissections) against a blood vessel wall. In certain arrangements, the device 1 can be used to deliver one or more implants that can be used to treat dissections or residual stenosis in non-calcified, moderately calcified or severely calcified lesions.

A variety of delivery methodologies and devices can be used to deploy embodiments of the implants described herein, some of which are described herein. For example, the implant(s) according to any of the embodiments described herein can be delivered into the blood vessel with an endovascular insertion. The delivery catheters for the different embodiments of implants can be different or the same and can have features specifically designed to deliver the specific implant. As noted above, the delivery device 1 may be used to deliver a variety of different implants and is not limited to use with the specific implants illustrated or described herein. FIGS. 3 and 3A illustrate an example of an implant that can be used with the delivery device 1 and the method of use shown and described with reference to FIGS. 11-15. FIGS. 11-15 illustrate another example of an implant that can be used with the delivery device 1 and that includes apexes that are bent or turned upwards or radially outwards. The same numeral 2 has been used for different embodiments of implants in the figures for simplicity even though the implants may not include identical features (e.g., bent vs. non-bent apexes).

As has been mentioned, an angioplasty procedure or other type of procedure can be performed in a blood vessel. The angioplasty may be performed on a diseased or obstructed portion of the blood vessel. The diseased vessel can first be accessed with a cannula, and a guidewire advanced through the cannula to the desired location. An angioplasty balloon catheter carrying a balloon is advanced over the guidewire into a blood vessel in a location containing an obstruction formed by plaque. The balloon can then inflated at the desired location to compress the plaque and widen the vessel. The balloon can then be deflated and removed.

While widening the vessel, a dissection 114 of the plaque may be caused by the angioplasty. An angiogram can be performed after the angioplasty to visualize the vessel where the angioplasty was performed and determine if there is evidence of post-angioplasty dissection or surface irregularity. The delivery device 1 can be used to deliver an implant that can be used to secure the plaque dissection 114 or other surface irregularity (for example, a remaining stenosis or narrowed portion of the vessel) to the lumen wall 117 where needed.

Figure 11:
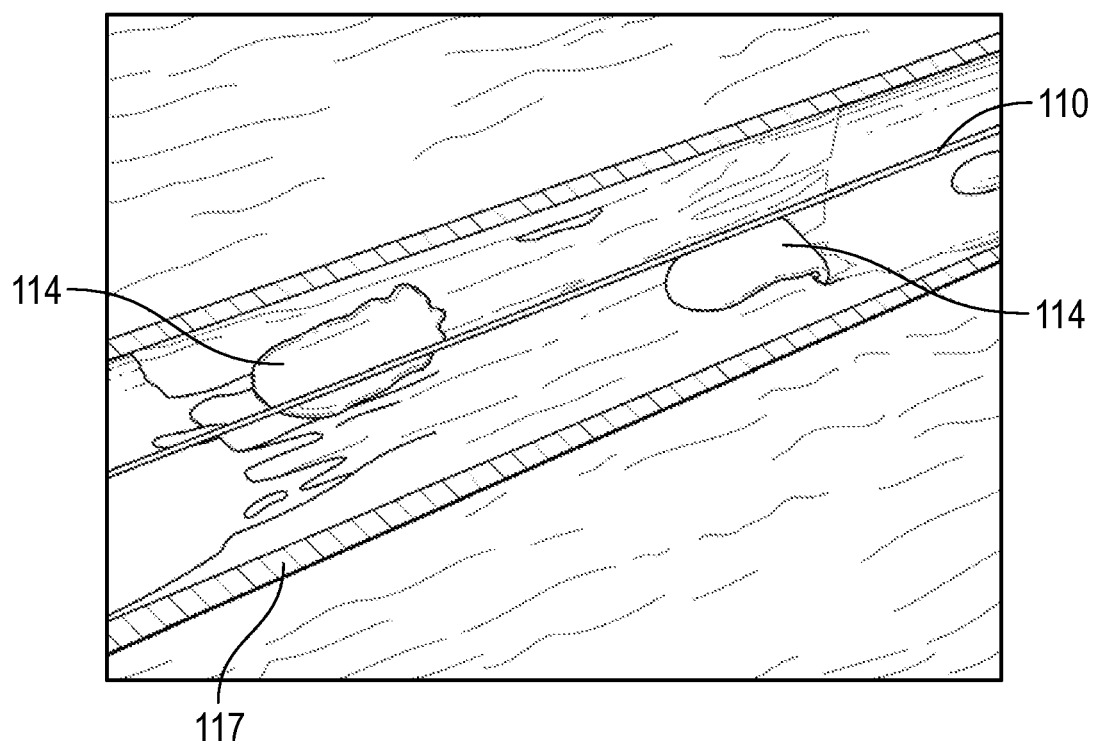
FIGS. 11-15 illustrate an example of a method of use of the delivery device of FIG. 1.
Figure 12:
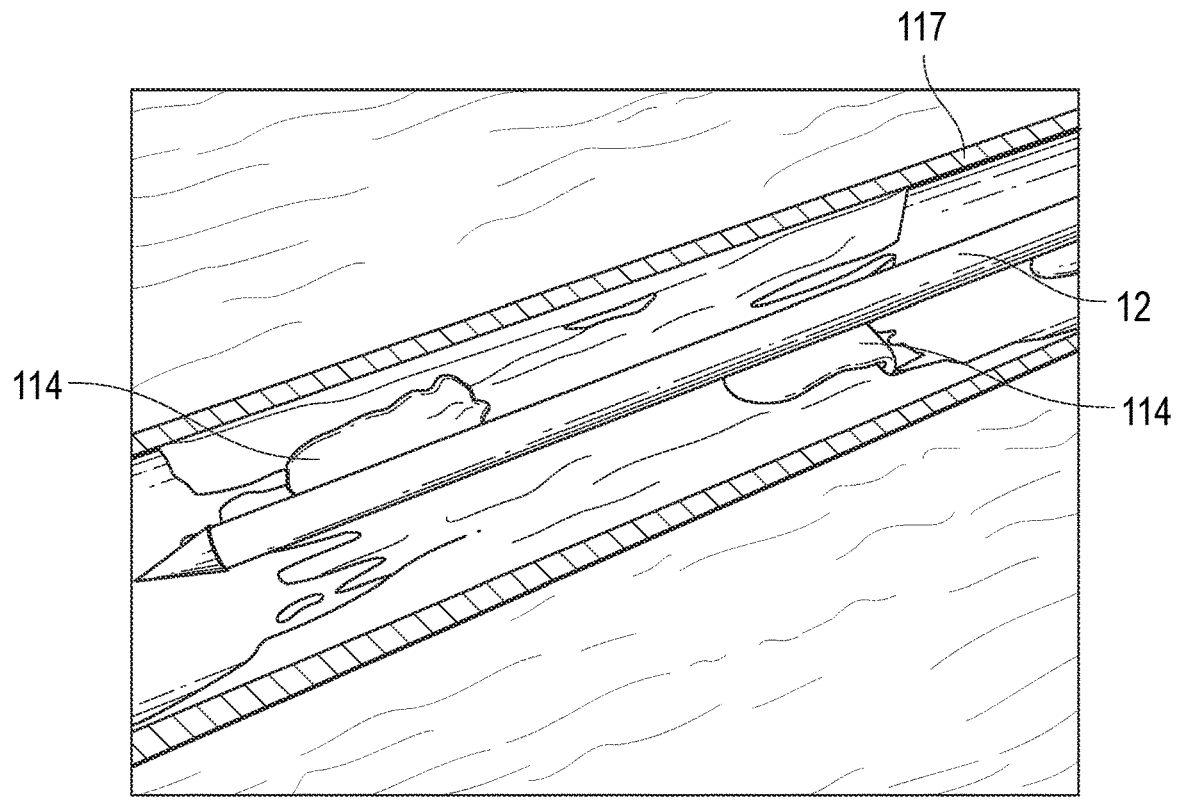
Figure 13:
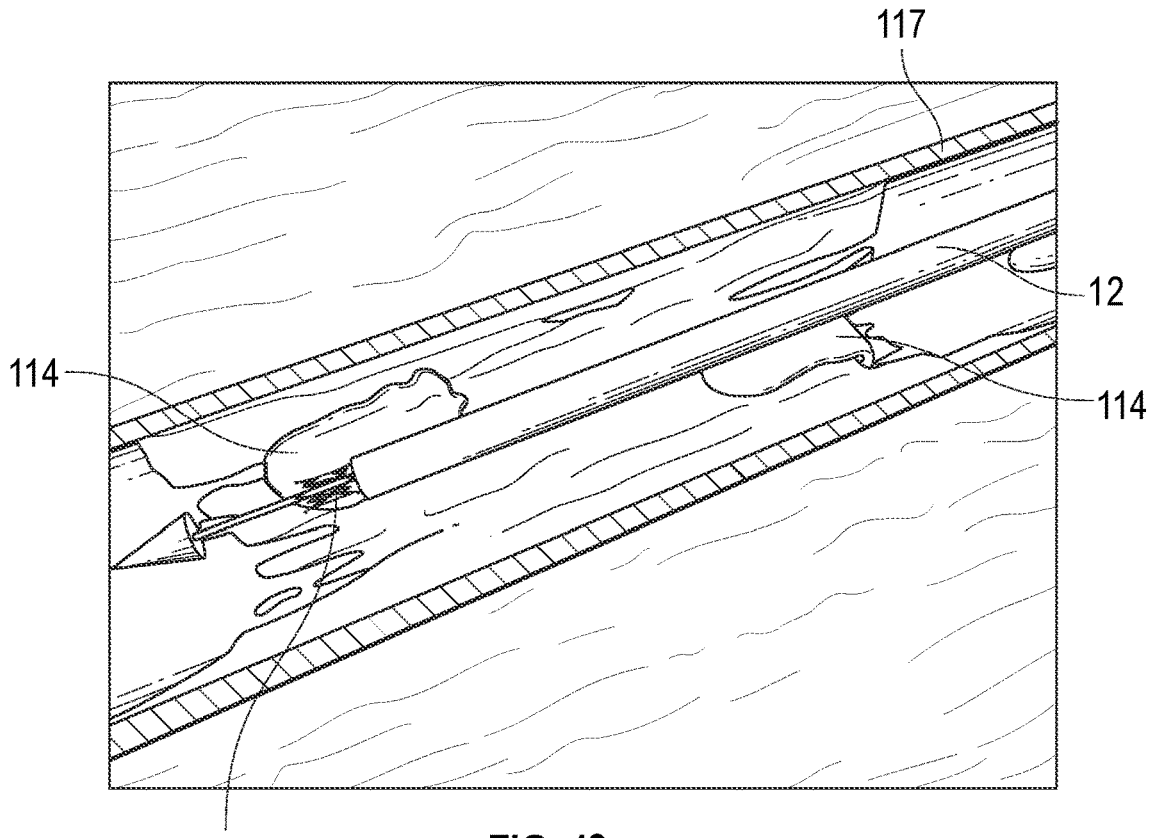
Figure 14:
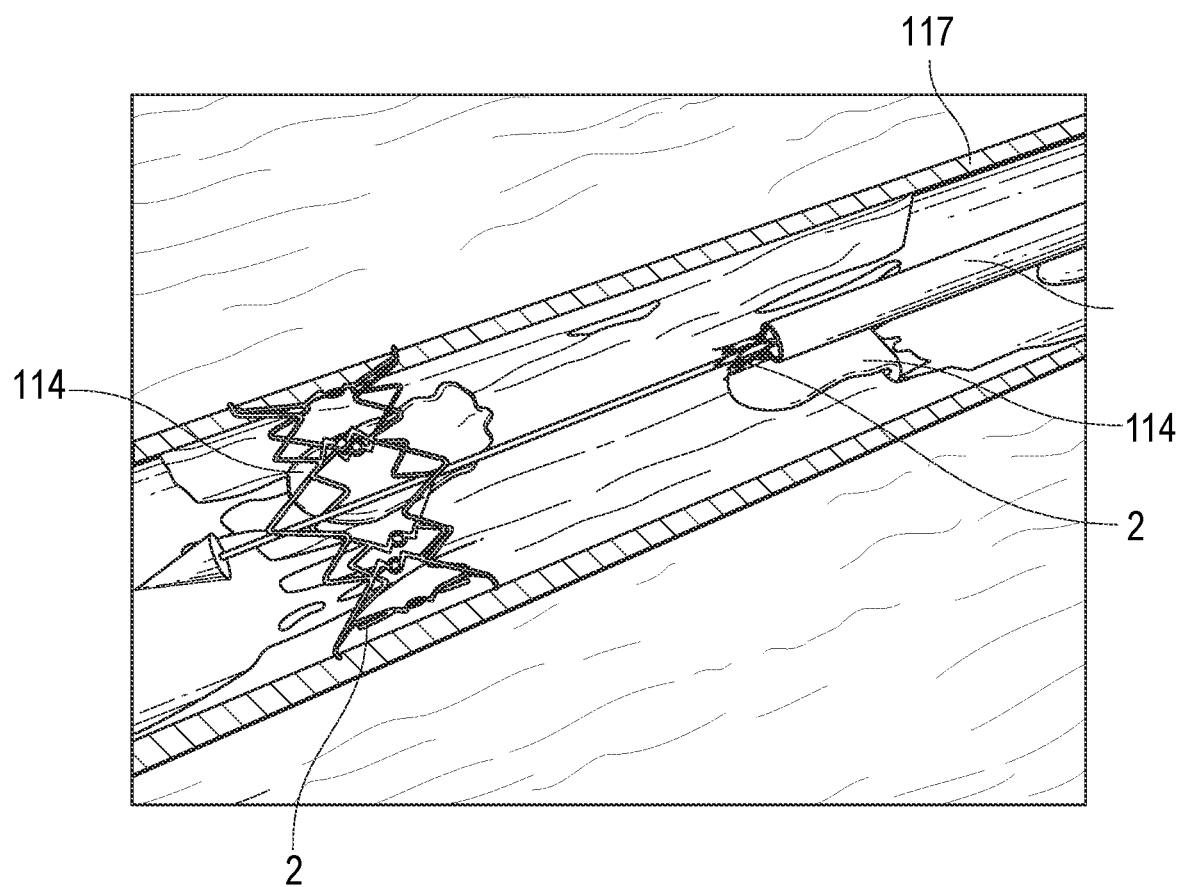

The delivery catheter 1 preloaded with one or more implants 2 according to one or more of the embodiments described herein (or other implants not illustrated or described herein) can be advanced through the vessel 117 and along the guidewire to the treatment site (FIG. 11). In some implementations, a new or separate guidewire and cannula can be used. A distal most marker, either on the catheter assembly 11 or on the distal most implant, can be positioned under visualization at the treatment location. The outer sheath 12 can be withdrawn, exposing a portion of the implant 2. As has been discussed, the outer sheath 12 can be withdrawn until a set point and then the position of the device 1 within the vessel can be adjusted, if necessary, to ensure precise placement of the implant 2 (FIG. 12). The set point can be for example, right before uncovering any of the implants, uncovering a portion or all of a ring, uncovering a ring or other marker visualized using imaging, etc.

The implant 2 can then be released in the desired location in the vessel lumen. As discussed previously, simultaneous placement can result upon release of some embodiments of the implant 2. Additional implants 2 can optionally then be placed as desired (FIG. 13) in a distal to proximal placement within the treatment segment of the vessel.

In some embodiments of the disclosure, the precise placement of the implants 2 can be set upon positioning of the device 1 within the vessel 117 based on the position of a marker on the catheter assembly 11 and/or the implant 2. Once positioned, one or more implants can then be deployed while maintaining the inner shaft 26 in place and slowly retracting the outer sheath 12.

Upon placement of the second implant 2, an intravascular construct is formed in situ. The in situ placement can be in any suitable vessel, such as in any peripheral artery. The construct need not be limited to just two implants 2. In fact, a plurality of at least three, four, five, six or more intravascular implants 2 (or any of the other implants herein) can be provided in an intravascular construct formed in situ. In one embodiment each of the plurality of implants has a length of no more than about 14 mm. In one configuration, at least one of, e.g., each of, the implants are spaced apart from an adjacent implant by at least about 4 mm, or between about 4 mm and 8 mm or between about 6 mm and 14 mm. Although certain embodiments of implants have a length of 12 mm or less, other embodiments of implants can be longer, e.g., up to about 15 mm long. Also, neighboring implants 10 can be positioned as close as 4 mm apart, particularly in vessels that are less prone to bending or other movements. In the various delivery devices/catheters described herein, the spacing between implanted implants can be controlled to maintain a set or a minimum distance between each implant. As can be seen, the delivery catheters and/or implants can include features that help maintain the desired distance between implants. Maintaining proper inter-implant spacing can help ensure that the implants are distributed over a desired length without contacting each other or bunching up in a certain region of the treated vessel. This can help to prevent kinking of the vessel in which they are disposed.

While a one, two, or three implant construct formed in situ may be suitable for certain indications, an intravascular construct having at least 4, 5, or at least 6 intravascular implants may be advantageous for treating loose plaque, vessel flaps, dissections or other maladies that are significantly longer. For example, while most dissections are focal (e.g., axially short), a series of dissections may be considered and treated as a more elongated malady.

Figure 15:
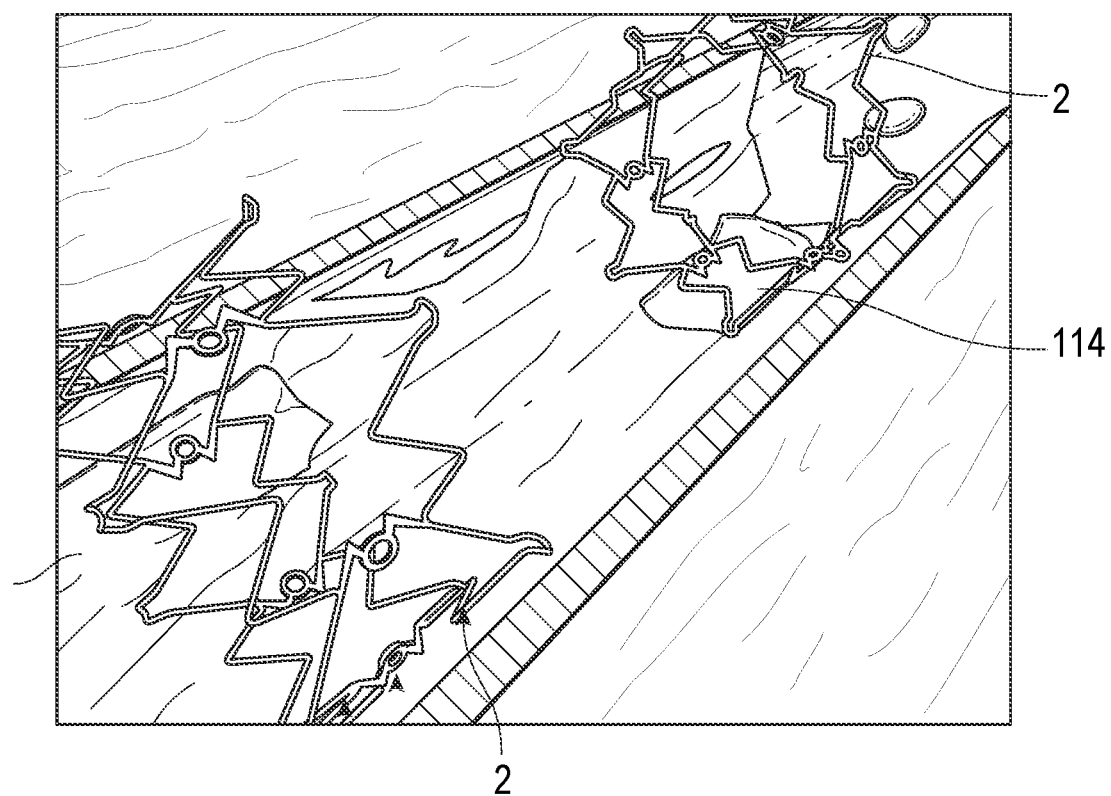

Optionally, once the implants 2 are in place, the angioplasty balloon can be returned to the treatment site and inflated to expand the implants 2 to the desired state of expansion. FIG. 15 shows the implants 2 in their final implanted state.

The delivery device 1 can be used to deliver more than one intravascular implant accurately in positions along the length of a plaque accumulation site where specific outward expansion forces are needed to stabilize the site and/or hold a dissection and/or pieces of loose plaque out of the way of blood flow and/or to expand portions of the site where the vessel remain narrowed. By using a series of implants, over-scaffolding of the vessel can be avoided. A reduction in cellular response is believed to be achieved partly through a reduction of surface area contact between the implant and the blood vessel lumen as compared to using a single stent across the same treatment area.

In several embodiments of the disclosure, one purpose of the implants described herein, as distinct from traditional stenting, is to reduce the amount of implanted foreign material to a minimum while still performing focal treatment of the blood vessel condition so as to cause a minimum of blood vessel wall reaction and adverse post-treatment restenosis. The implant can be designed to have substantially less metal coverage and/or contact with the blood vessel surface, thereby inciting less acute and chronic inflammation. Reduced contact area of implanted material against the blood vessel wall is correlated with a lower incidence of intimal hyperplasia and better long-term patency. Substantially reduced length along the axial distance of the blood vessel permits a more targeted treatment, correlates with less foreign body coverage of the blood vessel surface, avoids covering portions of the surface that are not in need of coverage, and correlates with both early and late improved patency of blood vessel reconstructions.

The delivery device 1 can be used to deploy an implant only where needed to tack down plaque that has been disrupted by balloon angioplasty or other mechanisms and/or or to expand portions of the vessel that are subjected to residual stenosis after balloon dilations, for example, in more calcified lesions. Advantageously, in several embodiments of the disclosure, rather than cover an entire area of treatment, the delivery device can be used to place more than one implant locally without overlap and selectively, for example, not extending into normal or less diseased artery segments. This permits the blood vessel to retain its natural flexibility because there is minimal to no scaffolding when a small profile implant is used locally or even when multiple implants are spaced apart over the length of treatment.

While useful, the embodiments of delivery devices described herein are often described in the context of delivering implants for holding loose plaque and/or arterial tissue (dissections) against a blood vessel wall, certain advantages and features of the embodiments disclosed herein can find utility in other applications such as, for example, medical applications in which it is desirable to deliver one or more implants to create or preserve unobstructed blood flow in a blood vessel or to address deformations or dissections in other body lumens or passages or cavities or to address calcified lesions.

E. Conclusion and Terminology

While the methods and devices described herein may be susceptible to various modifications and alternative forms, specific examples thereof have been shown in the drawings and are described in detail herein. It should be understood, however, that the inventive subject matter is not to be limited to the particular forms or methods disclosed, but, to the contrary, covers all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein.

In some embodiments of the disclosure, the systems or devices comprise various features that are present as single features (as opposed to multiple features). For example, in one embodiment, the delivery device includes a single unitary housing instead of multiple housing parts and/or a single unitary thumbwheel instead of multiple thumbwheel parts. A single implant and/or a single radiopaque marker band (or other means for facilitating visualization) may also be included. Multiple features or components are provided in alternate embodiments. Additionally, the structures described herein can be embodied as integrated components or as separate components.

In some embodiments of the disclosure, the systems or devices comprise one or more of the following: means for controlled mechanical implant deployment (e.g., a belt/pulley assembly), different means for manual re-sheathing and un-sheathing after initial implant deployment (e.g., re-sheath rack, re-sheath button, and re-sheath housing or handle), means for locking out operation of the deployment mechanism, etc.

In any methods disclosed herein, the acts or operations can be performed in any suitable sequence and are not necessarily limited to any particular disclosed sequence and not be performed in the order recited. Various operations can be described as multiple discrete operations in turn, in a manner that can be helpful in understanding certain embodiments of the disclosure; however, the order of description should not be construed to imply that these operations are order dependent. The section headings used herein are merely provided to enhance readability and are not intended to limit the scope of the embodiments disclosed in a particular section to the features or elements disclosed in that section.

For purposes of comparing various embodiments of the disclosure, certain aspects and advantages of these embodiments are described. Not necessarily all such aspects or advantages are achieved by any particular embodiment. Thus, for example, embodiments can be carried out in a manner that achieves or optimizes one advantage or group of advantages without necessarily achieving other advantages or groups of advantages.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z. Unless otherwise explicitly stated, articles such as 'a' or 'an' should generally be interpreted to include one or more described items.

The methods disclosed herein may include certain actions taken by a practitioner; however, the methods can also include any third-party instruction of those actions, either expressly or by implication. For example, actions such as "deploying a self-expanding implant" include "instructing deployment of a self-expanding implant." The terms "top," "bottom," "first," "second," "upper," "lower," "height," "width," "length," "end," "side," "horizontal," "vertical," and similar terms may be used herein; it should be understood that these terms have reference only to the structures shown in the figures and are utilized only to facilitate describing embodiments of the disclosure. The terms "proximal" and "distal" are opposite directional terms. For example, the distal end of a device or component is the end of the component that is furthest from the operator during ordinary use. A distal end or tip does not necessarily mean an extreme distal terminus. The proximal end refers to the opposite end, or the end nearest the operator during ordinary use. The ranges disclosed herein also encompass any and all overlap, sub-ranges, and combinations thereof. For example, description of a range such as from 50 to 250 cm should be considered to have specifically disclosed subranges such as from 50 to 100 cm, from 100 to 200 cm, from 150 to 250 cm etc., as well as individual numbers within that range, for example, 50, 80, 90, 95, 100, 70.5, 90.5 and any whole and partial increments therebetween. Ranges also include the numbers at the boundaries of the range. For example, the range of from 50 to 250 cm includes 50 cm and 250 cm. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 4 mm" includes "4 mm." Phrases preceded by a term such as "substantially" include the recited phrase and should be interpreted based on the circumstances (e.g., as much as reasonably possible under the circumstances).

What is claimed is:

1. A delivery device for delivering multiple implants, the device comprising:
    an inner shaft comprising a proximal end, a distal end, and a lumen extending from the proximal end to the distal end;
    an outer sheath having a proximal end, a distal end, and a second lumen extending from the proximal end of the outer sheath to the distal end of the outer sheath, the outer sheath being moveable relative to the inner shaft;
    a rotary deployment handle configured to cause movement of the outer sheath relative to the inner shaft so as to facilitate delivery of multiple implants carried by the inner shaft at spaced-apart locations along the inner shaft, wherein the rotary deployment handle comprises:
        a thumbwheel;
        a belt and pulley assembly operably coupled to the thumbwheel and to the outer sheath such that rotation of the thumbwheel in a first rotational direction causes movement of the outer sheath relative to the inner shaft;
        a lockout assembly configured to:
            (a) cause the thumbwheel to transition from a locked configuration in which the thumbwheel is unable to rotate to an unlocked configuration in which the thumbwheel is able to rotate and
            (b) tension the belt during the transition from the locked configuration to the unlocked configuration; and
        a re-sheath assembly configured to facilitate re-sheathing of the inner shaft by pulling a re-sheath housing that is coupled to the inner shaft in a proximal direction, thereby moving the inner shaft relative to the outer sheath;
    wherein the lockout assembly comprises a lockout lever, the lockout lever comprising a proximal end portion configured to extend out of a main housing of the rotary deployment handle when the lockout assembly is in a locked configuration and a distal end fixedly coupled to the main housing of the rotary deployment handle; and
    wherein the lockout assembly further comprises a lockout plate comprising a proximal abutment surface configured to interface with a protrusion of the lockout lever and multiple engagement members configured to interface with one or more recesses between a plurality of teeth of the thumbwheel so as to prevent rotation of the thumbwheel when the lockout assembly is in the locked configuration, wherein the lockout plate is biased to move toward a proximal end of the rotary deployment handle by a spring.

2. The delivery device of claim 1, further comprising a ratchet wheel configured to interact with the thumbwheel in such a manner so as to allow rotation of the thumbwheel in the first rotational direction but not in a second opposite rotational direction.

3. The device of claim 1, wherein, upon depression of the proximal end portion of the lever into the main housing by an operator, the lockout assembly transitions to an unlocked configuration by causing the protrusion of the lever to disengage from the proximal abutment surface of the lockout plate, thereby causing the lockout plate to move proximally so as to allow a proximal engagement member of the multiple engagement members of the lockout plate to disengage from the thumbwheel and thereby allow the thumbwheel to rotate.

4. The device of claim 1, wherein the re-sheath assembly comprises the re-sheath housing removably coupled to a proximal end of the main housing of the rotary deployment handle, a re-sheath button located adjacent the proximal end of the main housing distal to the re-sheath housing, and a re-sheath rack located within the main housing of the rotary deployment handle.

5. The device of claim 4, wherein the re-sheath button is configured to prevent longitudinal movement of the re-sheath housing and re-sheath rack unless the re-sheath button is pressed into the main housing by an operator.

6. A delivery device for delivering implants, the device comprising:
    an inner shaft comprising a proximal end and a distal end;
    an outer sheath having a proximal end, a distal end, and a lumen extending from the proximal end of the outer sheath to the distal end of the outer sheath, the outer sheath being moveable relative to the inner shaft;
    a deployment handle configured to cause movement of the outer sheath relative to the inner shaft so as to facilitate delivery of multiple implants carried by the inner shaft at spaced-apart locations, wherein the deployment handle comprises:
        an elongated main housing comprising a proximal end and a distal end and an upper surface;

a deployment actuator configured to cause the movement of the outer sheath relative to the inner shaft; and
a re-sheath assembly configured to facilitate re-sheathing of the inner shaft prior to removal of the delivery device from a treatment zone within a subject after deployment of one or more of the multiple implants at the treatment zone, wherein the re-sheath assembly comprises a re-sheath housing removably coupled to the proximal end of the main housing of the deployment handle, a re-sheath button located adjacent the proximal end of the main housing distal to the re-sheath housing, and a re-sheath rack located within the main housing of the deployment handle, wherein a proximal end of the re-sheath rack is fixedly coupled to the re-sheath housing and wherein the inner shaft is operably coupled to the re-sheath housing such that retraction of the re-sheath housing in a proximal direction away from the main housing causes the re-sheath rack and the inner shaft to move in a proximal direction, thereby re-sheathing the inner shaft within the outer sheath; wherein the deployment actuator comprises a thumbwheel extending out of the upper surface of the main housing, the thumbwheel comprising a plurality of teeth configured to engage with links of a belt that is operatively coupled to the outer sheath so as to effect movement of the outer sheath relative to the inner shaft when the thumbwheel is rotated; and wherein movement of the re-sheath rack in the proximal direction during re-sheathing causes the thumbwheel to transition to be placed in a locked configuration such that rotation of the thumbwheel is prevented during re-sheathing.

7. The device of claim 6, wherein the re-sheath button is configured to prevent longitudinal movement of the re-sheath housing and re-sheath rack unless the re-sheath button is pressed into the main housing by an operator.

8. The device of claim 6, further comprising a plurality of flush ports extending outward from the proximal end of the re-sheath housing to facilitate flushing of a lumen of the inner shaft and the lumen of the outer sheath.

9. The device of claim 6, wherein the inner shaft comprises a lumen extending from the proximal end to the distal end.

10. A method of delivering implants at multiple different treatment sites within a subject, the method comprising:
advancing a delivery catheter to a first treatment site within the subject, wherein the delivery catheter comprises an inner shaft and an outer sheath concentrically surrounding the inner shaft, wherein the inner shaft and the outer sheath are configured to move relative to each other, a deployment actuator configured to cause the movement of the outer sheath relative to the inner shaft, and wherein the inner shaft is loaded with a plurality of implants at spaced-apart locations along the length of the inner shaft;
wherein the deployment actuator comprises a thumbwheel extending out of an upper surface of a main housing of a rotary deployment handle, the thumbwheel comprising a plurality of teeth configured to engage with links of a belt that is operatively coupled to the outer sheath so as to effect movement of the outer sheath relative to the inner shaft when the thumbwheel is rotated;
deploying a first implant of the plurality of implants at the first treatment site within the subject by un-sheathing the first implant of the plurality of implants by moving the outer sheath proximally while the inner shaft remains stationary, re-sheathing a portion of the inner shaft corresponding to the locations of the deployed first implant of the plurality of implants by moving the inner shaft proximally while the outer sheath remains stationary, thereby facilitating improved safety to the subject while the delivery catheter is moved to a second treatment site within the subject, wherein said re-sheathing is effected by an operator pulling a re-sheath assembly of the rotary deployment handle in a proximal direction;
wherein the re-sheath assembly comprises a re-sheath housing removably coupled to the proximal end of the main housing of the rotary deployment handle, a re-sheath button located adjacent the proximal end of the main housing distal to the re-sheath housing, and a re-sheath rack located within the main housing of the rotary deployment handle, wherein a proximal end of the re-sheath rack is fixedly coupled to the re-sheath housing; wherein movement of the re-sheath rack in the proximal direction during re-sheathing causes the thumbwheel to transition in a locked configuration such that rotation of the thumbwheel is prevented during re-sheathing;
advancing the delivery catheter to the second treatment site within the subject;
un-sheathing the portion of the inner shaft corresponding to the locations of the deployed first implant of the plurality of implants by moving the inner shaft distally while the outer sheath remains stationary such that a distal end of the outer sheath is at the same distance away from a distal end of the inner shaft as it was after deployment of the first implant of the plurality of implants, wherein said un-sheathing, of the portion of the inner shaft after delivery catheter is advanced to the second treatment site, is effected by the operator pushing the re-sheath housing of the rotary deployment handle in a distal direction; and
deploying a second implant of the plurality of implants at the second treatment site within the subject by un-sheathing the second implant of the plurality of implants by moving the outer sheath proximally while the inner shaft remains stationary.

11. The method of claim 10, wherein the plurality implants comprise self-expandable endovascular implants.

12. The method of claim 10, wherein the first treatment site is a location of one or more first vascular dissections and wherein the second treatment site is a location of one or more second vascular dissections.

13. The method of claim 10, wherein the first treatment site is in a first artery and wherein the second treatment site is in a second artery.

14. The method of claim 10, wherein the first treatment site and the second treatment site are each located above the knee of the subject.

15. The method of claim 10, wherein said un-sheathing is effected by rotation of the thumbwheel of the rotary deployment handle of the delivery catheter by an operator.

* * * * *